US005824535A

United States Patent [19]
Kou et al.

[11] Patent Number: 5,824,535
[45] Date of Patent: Oct. 20, 1998

[54] IDENTIFICATION, PURIFICATION AND DETECTION OF WSBV (BACULOVIRUS ASSOCIATED WITH WHITE SPOT SYNDROME)

[76] Inventors: Guang-Hsiung Kou, Department of Zoology, National Taiwan University; Chung-Hsiung Wang, Department of Plant Pathology and Entomology, National Taiwan University; Chu-Fang Lo, Department of Zoology, National Taiwan University, all of Taipei, Taiwan

[21] Appl. No.: 587,670

[22] Filed: Jan. 17, 1996

[51] Int. Cl.$^6$ ........................................................ C12N 7/02
[52] U.S. Cl. .......................................... 435/239; 435/235.1
[58] Field of Search .................................. 435/5, 6, 91.2, 435/235.1, 239; 536/23.72, 24.32, 24.33; 935/6, 8, 78

[56] References Cited

PUBLICATIONS

Lo et al. Diseases of Aquatic Organisms (Dec. 1996) 27: 215–225.
Durand et al, Diseases of Aquatic Organisms (Oct. 1996) 27: 59–66.
Chang et al., "Purification and Amplification of DNA from Penaeus monodon–Type Baculovirus (MBV)", Journal of Invertebrate Pathology 62:116–120, 1993.
Francki et al., "Classification and Nomenclature of Viruses", Fifth Report of the Int'l Committee on Taxonomy of Viruses, 117–123.
Johnson, "Rod–Shaped Nuclear Viruses of Crustaceans: Hemocyte–infecting Species", Diseases of Aquatic Organisms 5:111–122, 1988.
Johnson et al., "Rod–Shaped Nuclear Viruses of Crustaceans: Gut–infecting Species", Diseases of Aquatic Organisms 5:123–141, 1988.
Kim et al., "Molecular Phylogeny of Selected Decapod Crustaceans Based on 18S rRNA Nucleotide Sequences", Journal of Crustacean Biology 10:1–13, 1990.
Lester et al., "Light and Electron Microscope Evidence of Baculovirus Infection in the Prawn *Penaeus Plebejus*", Diseases of Aquatic Organisms 3:217–219, 1987.
Lightner et al., "Observations on the Geographic Distribution, Pathogenesis and Morphology of the Baculovirus From *Penaeus Monodon* Fabricius", Aquaculture 32:209–233, 1983.
Mari et al., "Preliminary Characterization and Partial Cloning of the Genome of a Baculovirus from *Penaeus Monodon* (PmSNPV=MBV)", Diseases of Aquatic Organisms 16:207–215, 1993.

Oste et al., "Product Application Focus Polymerase Chain Reaction", Biotechniques 6:162–167, 1988.
Shengli et al., "Epidemiological Studies on the Explosive Epidemic Disease of Prawn in 1993–1994", Journal of Fisheries of China, 19:112–119, 1995.
Sano et al., "Baculovirus Infection of Cultured Kuruma Shrimp, *Penaeus Japonicus* in Japan", Fish Pathology 15:185–191, 1981.
Sano et al., "Baculoviral Mid–gut Gland Necrosis (BMN) of Kuruma Shrimp (*Penaeus Japonicus*) Larvae in Japanese Intensive Culture Systems", Helgolander Meeresunters 37:255–264, 1984.
Takahashi et al., "Electron Microscopic Evidence of Bacilliform Virus Infection in Kuruma Shrimp (*Penaeus Japonicus*)", Fish Pathology 29:121–125, 1994.
Wongteerasupaya et al., "A Non–occluded, Systemic Baculovirus that Occurs in Cells of Ectodermal and Mesodermal Origin and Causes High Mortality . . . ", Diseases of Aquatic Organisms 21:69–77, 1995.
Cai et al., J. Fish. China, 16: 112–117, 1995.
ShrimProbe™ Brochure, DiagXotics, Wilton, CT.
Nakano et al., Fish Pathology, 29 (2): 135–139, 1994.
Momoyama et al., Fish Pathology, 29 (2): 141–148, 1994.
Inouye et al., Fish Pathology, 29 (2): 149–158, 1994.
Lightner, Boca Raton, pp. 393–486, 1993.
Chang et al., Fish Pathol., 27 (3): 127–130, 1992.
Francki et al., Arch. Virol., suppl. 2: 1–450, 1991.
Bruce et al., J. Virol. Methods, 34: 245–254, 1991.
Erlich et al., Nature, 331: 461–462, 1989.
Lightner et al., J. Invertebr. Pathol., 38: 299–302, 1981.
Couch, Nature, 247 (2438): 229–231, 1974.
Couch, J. Invertebr. Pathol., 24: 311–331, 1974.

*Primary Examiner*—Carla J. Myers
*Attorney, Agent, or Firm*—Fish & Richardson P.C.

[57] ABSTRACT

This invention relates to the identification, purification and detection of a new infectious viral agent in arthropods, especially shrimps. The virus is named as WSBV (Baculovirus associated with white spot syndrome). Two WSBV genomic DNA libraries were constructed and based upon the sequence of one of the cloned WSBV DNA fragments, a WSBV specific primer set for PCR to detect the WSBV infection in penaeid shrimps has been developed. The results of the present invention provide an effective diagnostic tool for screening WSBV infection in animal host organisms, in particular shrimps, to prevent the further spread of this viral disease.

6 Claims, 18 Drawing Sheets

1    GTCGA CAGAC TACTA ACTTC AGCCT ATCTA GTAAA ACAAG CTAAA AGATT
                146 F1
51   CGACG GAGTT GACCC AGCCT TCCCT GCCGC CCTCA CCTGC GCTTC TCACC

101  TCATG CTTTC TTCCA TGGAT TCCCA TACAA AGTCA TCTTT CATGG ACAAC

151  ATCAA ATTGC ACATG ACTGA TACTC AATGC TTCTT CAAGA ACATT GAACG

201  ATTTG AGAAA TTCTT GGGAA GATAT GGGGA CGAAT ACGCC ATGTC CCACA

251  AGCAA AATTG TAACT GCCCC TTCCA TCTCC ACCAC ACTTT TACTC CCTCA
                146 F2
301  GATAA CGAGC ATCTG GTATC CTCTT TCGCA TTCGC CCGCC CAGAA GTCTC

351  CATGG AAGAA ATTAG AGCCA CACCC TATCA GGCCA ACAAG CTTAT TAGTG

401  ACAAA CATTA CGTGA TGAAC ATGTC CAAGA TCGAT TCTAG AGTAA CAGGA

451  TCTTC CCTCC TTAAG AAGGT TAGCC AATGG ACTGA AATGA GAATG AACTC

501  CAACT TTAAT GGAAC ATTTG AACCA TCAAG ACTCG CCCTC TCCAA CTCTG

551  GCATG ACAAC GGCAG GAGTC AACCT CGACG TTATT GTCAA ACCAA ATAAT

601  GCAAG AAGTG TACTA GGAAT ATTGG AATGT CATCG CCAGC ACGTG TGCAC

651  CGCCG ACGCC AAGGG AACTG TCGCT TCAGC CATGC CAGCC GTCTT CCAGG

701  CAACC GATGG AAACG GTAAC GAATC TGAAC TGATC CAGAA TGCTC TGCCA

751  AGGAA CAGAT ACATC CAAAA GAGCA CAATG AACGC TCAAA CTGTC GTGTT

801  TGCTA ATGTT TTGGA ACAAC TTATC GCCGA TCTTG GAAAG GTTAT CGTGA

851  ACGAA CTGGC CGGCA CCATC GCTGA ATCTG TACCA GAAAG CGTAT ATGAA

901  AACAC CAAGG AAATG ATTGA TAGAC TAGGC TCTGA CGACC TCTTC AAATC

951  TAATA ATAAT GGAGG AGTAG AATCA ATGGA TTATG AAGAT AGCGA AACAA

1001 CATCC AACAA TGGTC CCGTC CTCAT CTCAG AAGCC ATGAA GAATG CCGTC

1051 TATCA CACAC TAATT TCCGG CAAGG CAGCT CGCCC GGAAA ATGTA CCATT

1101 CGCCT CATGC GCCAG CGGCC CTCTC GCCTT TGATT TCCTT CTGTC AAAGG

1151 GAGAT ACATT CGAAG AAAAG AACGC CGAAC AAGGT GCAGC AGCTG CCGTA
                                    (146 R2)    tg ttcca cgtcg tcgac ggcat
1201 TCCTC TACCT ATTCT TCCTC TTCTA ACACT ACTCT TCGTA AGCAT TTGGC
                                                                      EcoR1
1251 TCGAG TTTTC GAAGC CATCT CTAAG CAAGT AACTG ATGCT GAATT CAAGG 1301 ATATC CTCAA CGATA TCGAA CGTAA TATTT CTTCT GACTA TACTA ACTGT
                                                            EcoR1
1351 CCACC AAATA CTAAC CAAAA TGCCT TTGCT CTAGC TATCA AGACA GAATT 1401 CAGCA GAATT GTTTC CTTCT TAACC ATTCT TCGTA AGAAC ATTAC ACCCG
                                            (146 R1) 3'- agcat tcttg taatg tgggc
1451 CATTA GTCGA C
     gtaat-5'

FIG. 15C pms 146 primer set pms 146 F1 5' - ACT ACT AAC TTC AGC CTA TCT AG -3' pms 146 R1 5' - TAA TGC GGG TGT AAT GTT CTT ACG A -3' pms 146 F2 5' - GTA ACT GCC CCT TCC ATC TCC A -3' pms 146 R2 5' - TAC GGC AGC TGC TGC ACC TTG T -3' pms 146 F3 5' - TGG GAA GAT ATG GGG ACG AAT -3' pms 146 R3 5' - CGA AGA GTA GTG TTA GAA GAG GA -3' pms 146 F4 5' - AGA AGG TTA GCG AAT GGA CTG -3' pms 146 R4 5' - TTG AAG AGG TCG TCA GAG CCT -3' pms 146 F5 5' - GAA ACG TAA CG AAT CTG AAC TG -3' pms 146 R5 5' - CAG TCC ATT CGC TAA CCT -3' pms 146 R6 5' - CGT CCC CAT ATC TTC CCA -3'

FIG. 15D

IDENTIFICATION, PURIFICATION AND DETECTION OF WSBV (BACULOVIRUS ASSOCIATED WITH WHITE SPOT SYNDROME)

FIELD OF INVENTION

This invention relates to the identification, purification and detection of a new infectious viral agent in arthropods, especially shrimps. The virus is named as WSBV (Baculovirus associated with white spot syndrome).

BACKGROUND OF THE INVENTION

Recently, disease outbreaks have caused mass mortality among cultured penaeid shrimps in Asian countries. Since 1992, outbreaks of a new disease leading to serious mortality among populations of cultured kuruma shrimp (*Penaeus japonicus*) have occurred in northern Taiwan. The disease is characterized by obvious white spots on the carapace, appendages and the inside surface of the body, and cumulative mortality reaches 100% within 2–7 days. The diseased shrimps also display signs of lethargy and reddish coloration of the hepatopancreas. In 1993, white spot syndrome (W.S.S.) in cultured giant tiger prawn (*P. monodon*) and redtail prawn (*P. penicillatus*) was observed. Serious damage to penaeid shrimp production by W.S.S. in Taiwan has been reported (Tung et al. personal communication).

An epizootiological survey of kuruma shrimp in Japan reports similar findings (Nakano et al., Fish Pathology, 29 (2): 135–139, 1994). According to the evidence from electron microscopy and the results of challenge tests with the filtrate from diseased shrimp lymphoid organs, the causative agent was a virus that was temporarily designated RV-PJ, a rod-shaped nuclear virus of *Penaeus japonicus* (Inouye et al., Fish Pathology, 29 (2): 149–158, 1994; Takahashi et al., Fish Pathology, 29 (2): 121–125, 1994).

To date, the prevalence of baculoviruses in cultured penaeid shrimps has been well documented (Lightner et al., Aquaculture, 32: 209–233, 1983). Among these penaeid baculoviruses, monodon baculovirus (MBV), baculoviral mid-gut necrosis virus (BMNV) and Baculovirus penaei (BP) were considered to be the most important because they have on occasions caused serious losses in infected shrimp populations (Couch, Nature 247 (5438): 22–231, 1974; J. Invertebr. Pathol., 24: 311–331, 1974; Lightner & Redman, J. Invertebr. Pathology, 38: 299–302, 1981; Lightner et al. (1983), supra; Lightner et al., 1987; Sano et al., Fish Pathology, 15: 185–191, 1981).

Baculovirus-like viral particles were observed in the spontaneously diseased penaeid shrimp with W.S.S. (Tung et al., personal communication). This virus may possibly be the main causative agent for the W.S.S. that has occurred in Taiwan in penaeid shrimps. To prevent the spread of W.S.S. in shrimps, thereby rescuing the financial losses caused by this viral disease, it is necessary to identify the actual causative agent and then to develop a diagnostic method that is easy, accurate and not time-consuming in the detection of W.S.S. without sacrificing the whole subjects tested.

SUMMARY OF THE INVENTION

This invention is based on the finding of a new causative agent responsible for the incidence of white spot syndrome in penaeid shrimps. The causative agent has been isolated and purified and found to be a non-occluded rod-shaped virus particle, which is enveloped, 330±20nm in length and 87±7nm in diameter. This virus is determined to be a member of genus NOB (Non-Occluded Baculovirus) of the subfamily Nudibaculovirinae of Baculoviridae and the present isolate is designated as PmNOBIII, and as WSBV (Baculovirus associated with White Spot syndrome) to indicate PmNOBIII related agents. A WSBV genomic DNA library was constructed and based upon the sequence of one of the cloned WSBV DNA fragments, a WSBV specific primer set for PCR to detect the WSBV infection in penaeid shrimps has been developed. By PCR with the WSBV specific primer set, it was demonstrated that the causative agents of white spot syndrome in different shrimp species are in fact closely related. The results of the present invention provide an effective diagnostic tool for screening WSBV infection in animal host organisms, in particular shrimps, which tool may be extremely important in preventing the further spread of this viral disease. An easy, sensitive and specific ready-to-use diagnostic product, which includes primers established based on the nucleotide sequence of a unique genomic DNA clone derived from WSBV, can be developed for the detection of the presence of WSBV and to halt the further spread of this viral disease.

Features and advantages of the present invention will become apparent in the following detailed description of the preferred embodiments, with reference to the accompanying drawings, of which:

BRIEF DESCRIPTIONS OF THE DRAWINGS

Figure 5:
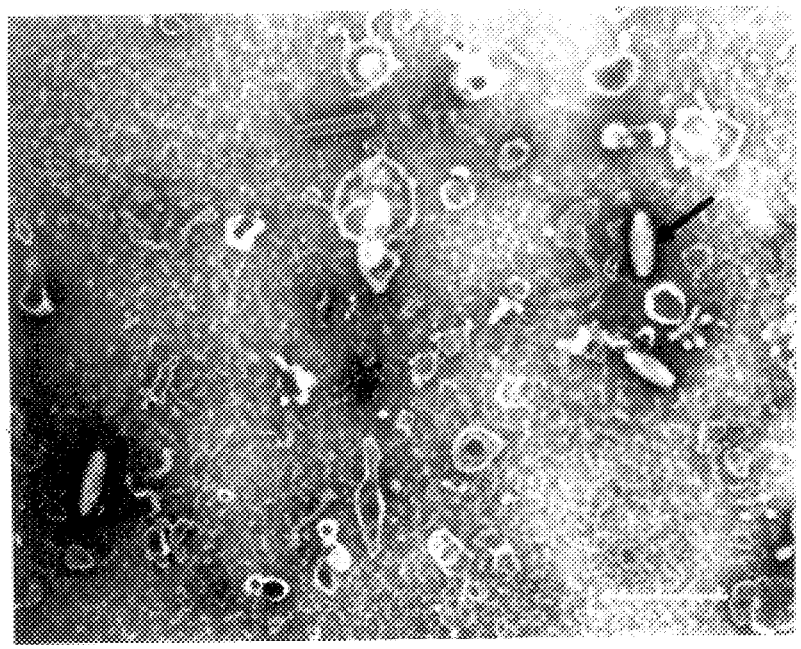

FIG. 5 is a negatively stained micrograph of the pellet from filtrate of diseased *P. monodon* epidermis. Virus particles (arrow) with rod-shape morphology were observed. Scale bar = 500 nm.

Figure 6:
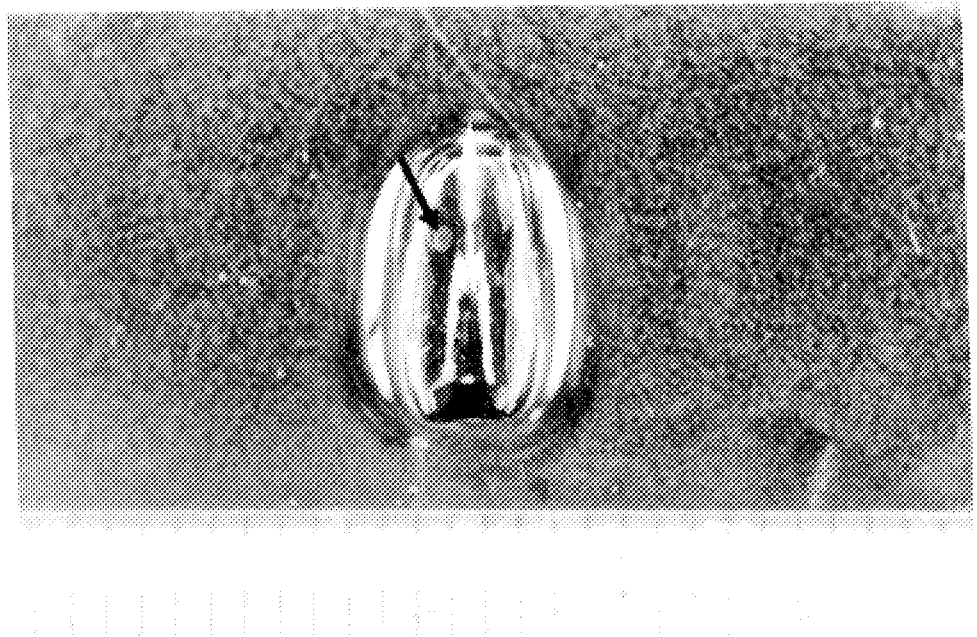

FIG. 6 displays the white spot (arrow) on the removed carapace of experimentally infected *P. japonicus*.

Figure 7:
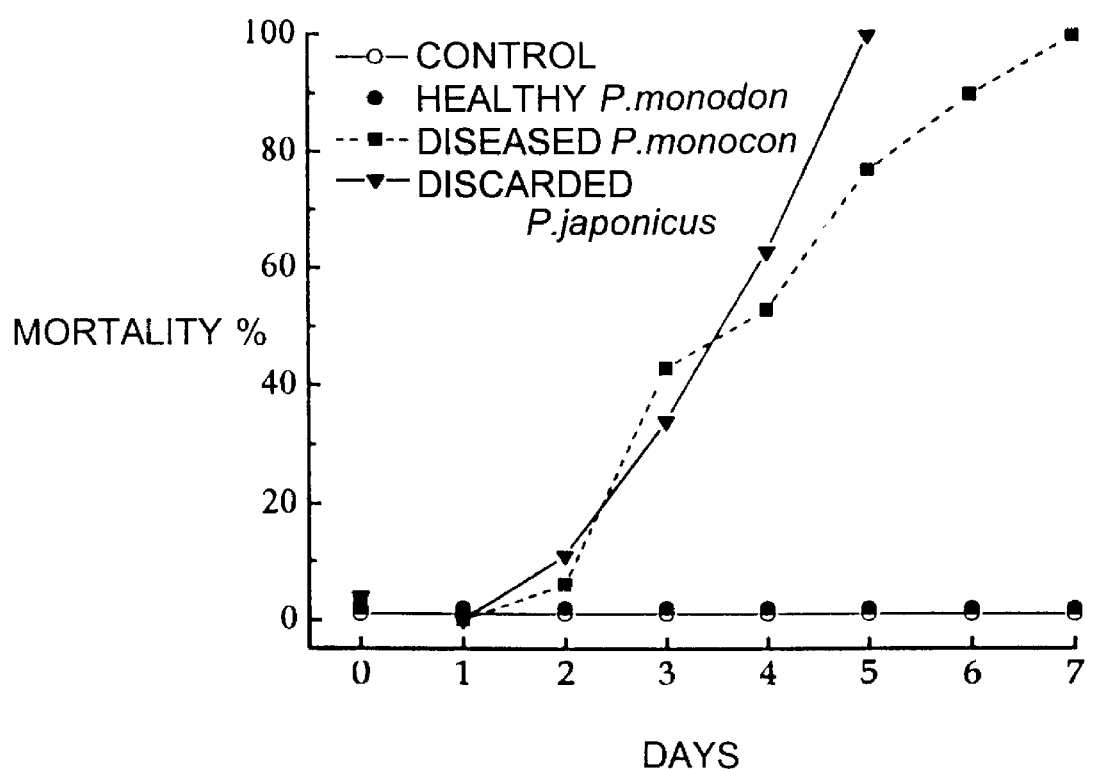

FIG. 7 shows the cumulative mortalities (%) of *P. japonicus* (0.08 g average weight) experimentally infected by immersion in filtrates from diseased *P. japonicus* and *P. monodon* contrasted with healthy shrimp control group(s).

Figure 8:
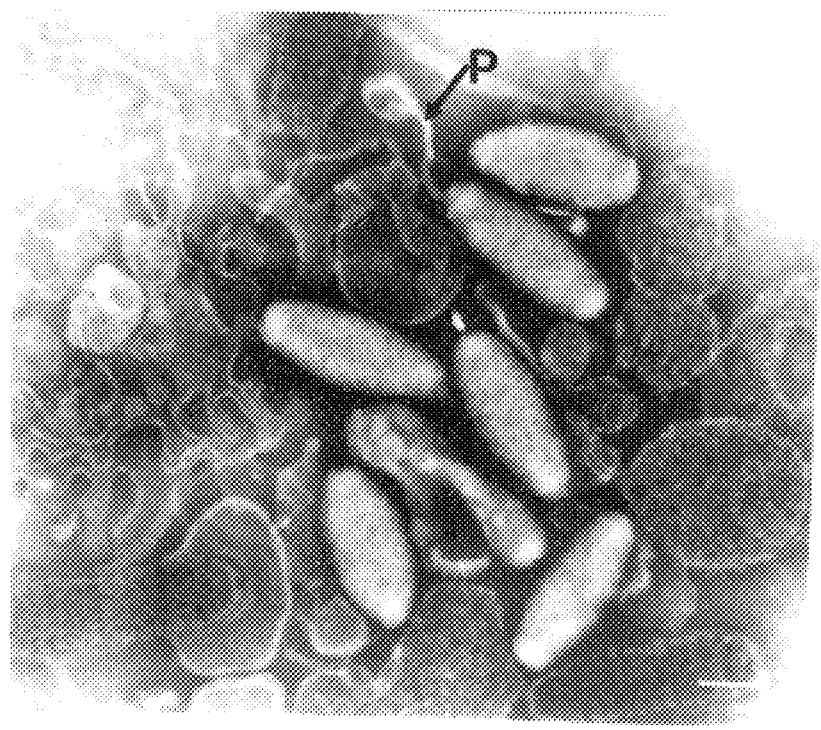

FIG. 8 is a transmission electron micrograph of negatively stained purified virions showing a tail-like projection (P) extending from one end of the virus. Bar: 0.1 mm.

Figure 9:
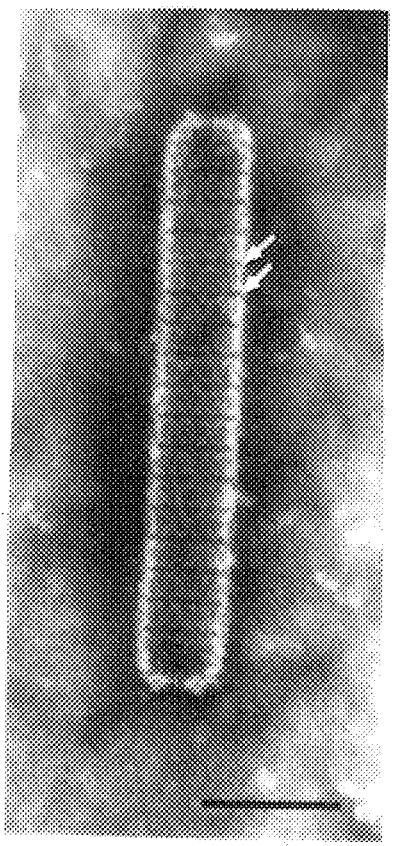

FIG. 9 is a transmission electron micrograph of Negatively stained non-enveloped nucleocapsid showing the cross-striations on the capsid formed by the ring subunits (arrows). The rings align perpendicularly to the longitudinal axis of the capsid. Bar: 0.1 mm.

Figure 10:
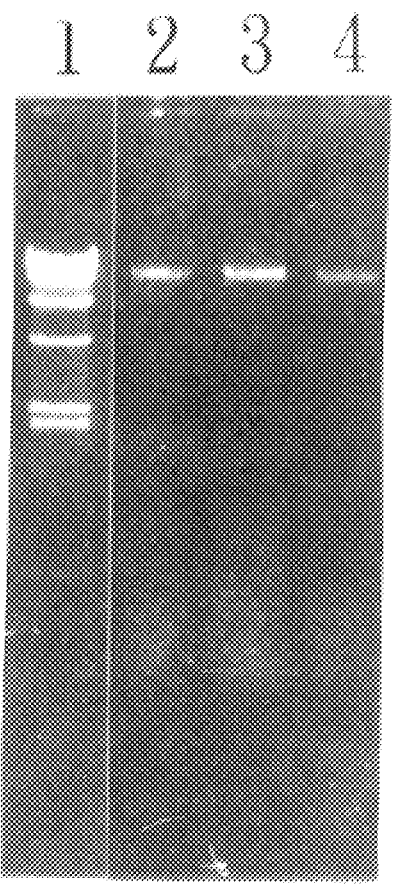

FIG. 10 shows an ethidium bromide-stained agarose gel of PmNOBIII DNA extracted from purified virions. A single molecule of DNA is observed in the gel. Lane 1: lamda phage DNA HindIII fragment marker; lanes 2–4: extracted PmNOBIII DNA from each of three respective preparations.

Figure 11:
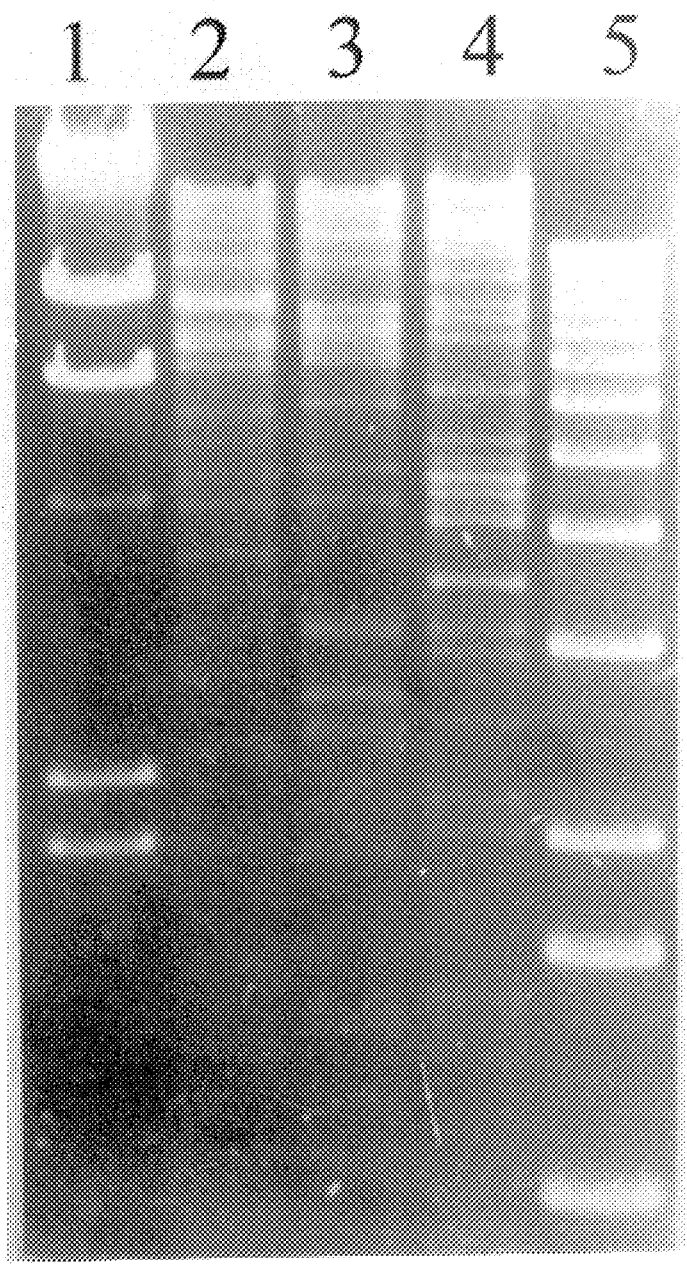

FIG. 11 shows an ethidium bromide-stained agarose gel of PmNOBIII DNA digested with three restriction endonucleases. At least twenty-two DNA fragments (arrows) can be identified in this gel. Lane 1: lamda phage DNA HindIII fragment marker; lane 2: PmNOBIII DNA HindIII fragments; lane 3: PmNOBIII DNA SalI fragments; lane 4: PmNOBIII DNA XhoI fragments; and lane 5: 1 Kb DNA Ladder.

Figure 12:
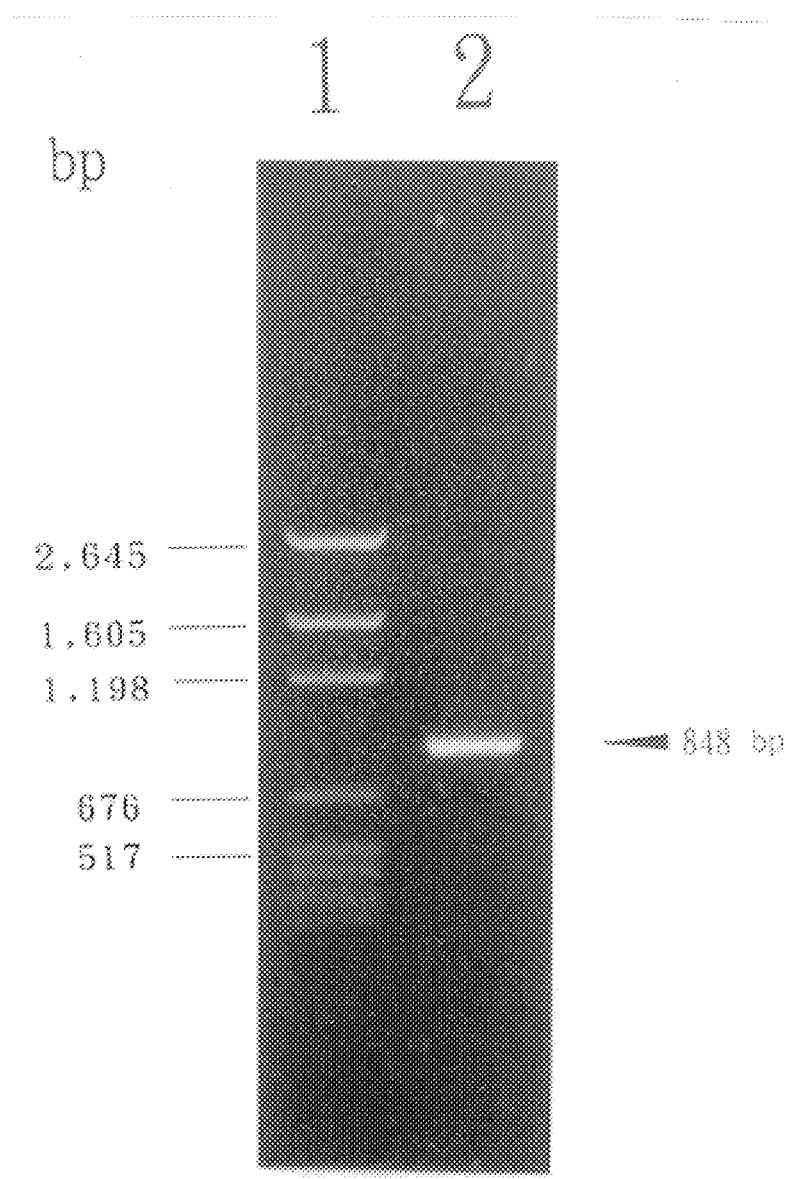

FIG. 12 shows an ethidium bromide-stained agarose gel of PCR-amplified 18S rDNA fragment from shrimp genomic DNA. Two primers for highly conserved regions of the 18S rRNA sequence of decapods, 143F and 145R, were used for the reaction and primed the amplification of the 848-bp fragment from DNA template prepared from the healthy *Penaeus monodon* (lane 2). Lane 1, PGEN DNA size marker. The size of DNA markers is indicated in base pairs (bp).

Figure 13:
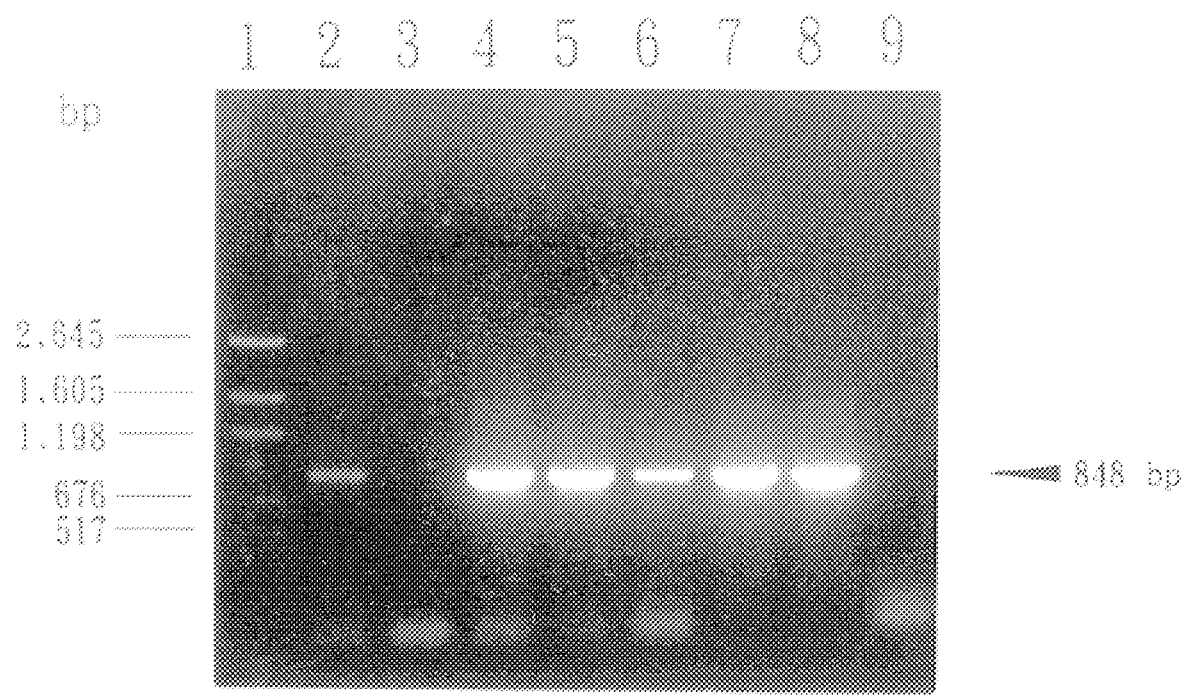

FIG. 13 shows a qualitative assessment using PCR and shrimp DNA specific primer set 143F and 145R, for monitoring shrimp DNA contamination in the WSBV genomic DNA preparations. The PCR products were analyzed on a 1% agarose gel. The shrimp DNA contamination is evidenced by the presence of a 848 bp PCR product. Lane 1, PGEN DNA size marker ; lanes 2–6, WSBV genomic DNA preparations as DNA template; lanes 7–8, shrimp genomic DNA prepared from healthy *Penaeus monodon* (lane 7) and *P. japonicus* (lane 8) as DNA template; lane 9: without DNA template. The size of the of DNA markers is given in base pairs (bp).

Figure 14:
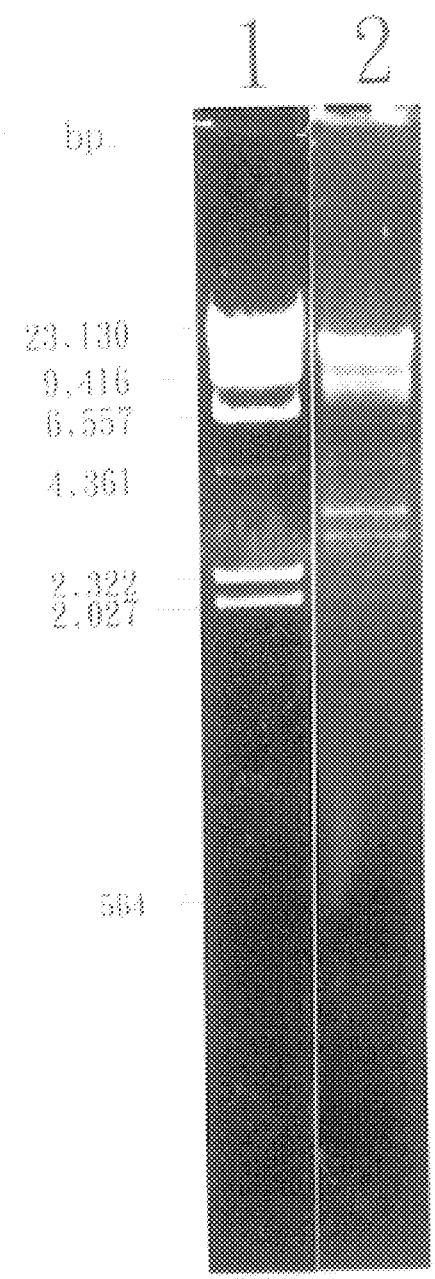

FIG. 14 shows the SalI digested WSBV DNA fragments. WSBV genomic DNA was digested with SalI restriction endonuclease at 37° C. for 3 hr. A 5-μl aliquot was analyzed on a 0.8% agarose gel containing ethidium bromide showing the fragments with a size from 15 kbp to less than 1 kbp (lane 2). From the same batch of digested DNA, a 20-μl aliquot was used for WSBV DNA library construction. Lane 1, lambda phage DNA HindIII fragment marker. The size of DNA markers is indicated in base pairs (bp).

Figure 15A:
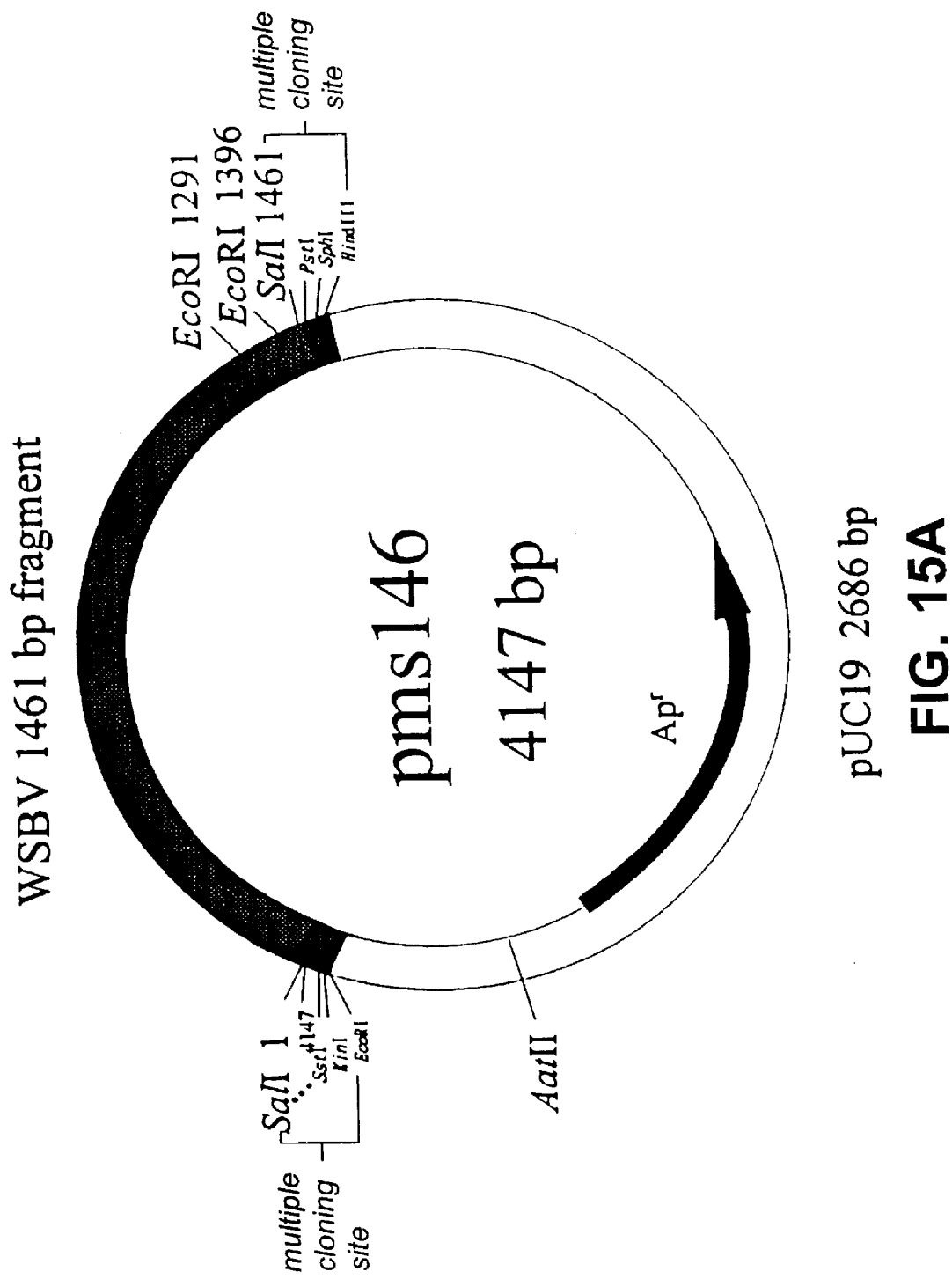
Figure 15B:
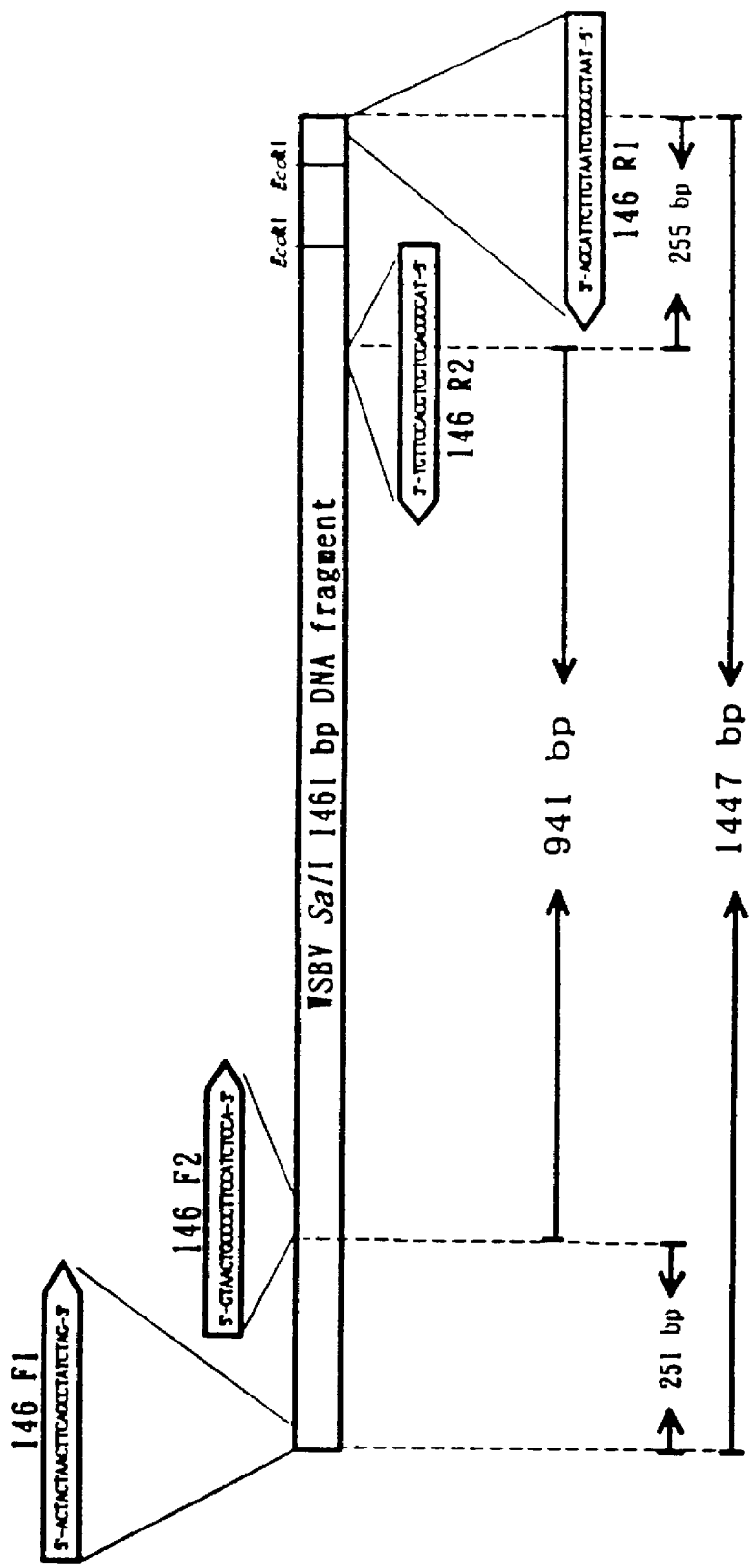

FIG. 15A displays a diagram of the SalI-1461 bp DNA fragment cloned in plasmid pms146 and FIG. 15B shows the locations of the primers, which are used for PCR amplication, in the SalI-1461 bp DNA fragment. The 146F1 and 146R1 prime the amplification of a 1447-bp fragment, while 146F2 and 146R2 prime the amplification of a 941-bp fragment. The positions of two EcoRI sites in SalI 1461 bp DNA fragment are also indicated. FIG. 15C shows the detailed nucleotide sequence of the SalI-1461 bp fragment, in which the locations of the two primer sets 146F1/146R1 and 146F2/146R2 and the two EcoRI sites are also indicated. FIG. 15D shows the nucleotide sequences of six primer sets developed from the SalI-1461 bp fragment.

Figure 16:

FIG. 16 shows the PCR amplification of WSBV and shrimp DNA specific fragments using DNA templates prepared from WSBV virions purified by sucrose gradient centrifugation. The WSBV specific primers 146F1 and 146R1 which yield a 1447-bp PCR product were used for reactions in lanes 2, 5, 8, and 11. The shrimp DNA specific primers 143F and 145R which yield a 848-bp PCR product were used for reactions in lanes 3, 6, 9, and 12. In lanes 4, 7, 10, and 13, all the primers 143F, 145R, 146F1 and 146R1 were added together in each of the reactions. The PCR products were analyzed on a 1% agarose gel. Lane 1, PGEN DNA size marker; lanes 2–4, PCR products using DNA template extracted from virions purified from diseased shrimp #1 epidermis showing shrimp DNA and WSBV DNA band; lanes 5–7, PCR product using DNA template extracted from virions purified from diseased shrimp #2 epidermis showing only WSBV DNA band; lanes 8–10, PCR product using DNA template extracted from virions purified from diseased shrimp #2 muscle showing intense shrimp DNA and WSBV DNA band; lanes 11–13, PCR product using DNA template extracted from healthy shrimp showing only shrimp DNA band. The size of DNA markers is indicated in base pairs (bp).

Figure 17:
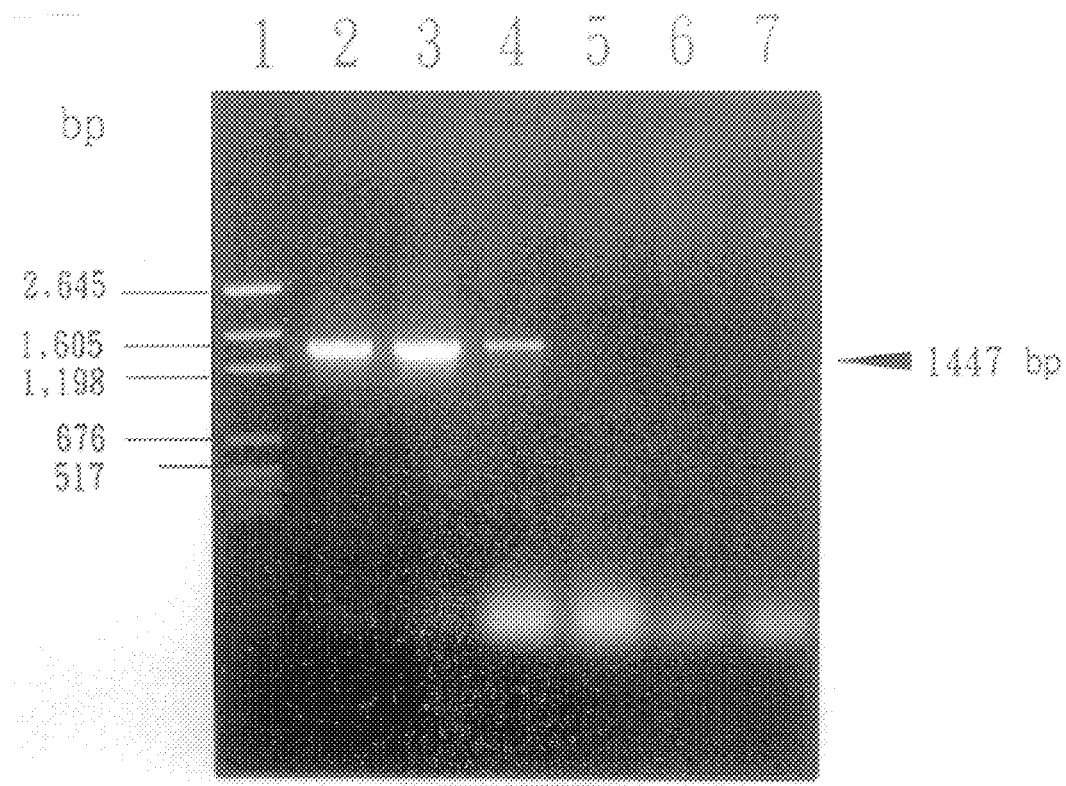

FIG. 17 shows the PCR amplification of WSBV and shrimp DNA specific fragments using plasmid pms146 and DNA extracts from *Penaeus monodon* naturally infected with WSBV as PCR DNA templates. The WSBV specific primers 146F1 and 146R1 were used for reactions in lanes 2, 5, 8 and 11. The PCR product is a 1447-bp fragment. Internal primers specific to 1447-kbp fragment, 146 F2 and 146 R2, were used for the reactions in lanes 3, 6, 9, and 12; they prime the amplification of a 941-kbp fragment. The shrimp DNA specific primers 143F and 145R were used for the reactions in lanes 4, 7, and 10. They prime the amplification of a 848-bp fragment. The amplification products were analyzed on a 1% agarose gel. Lane 1, pGEN DNA size marker); lanes 2–4, plasmid pms146; lanes 5–7, DNA extracts from naturally infected *P. monodon;* lanes 8–10, DNA extracts from naturally infected *P. japonicus;* lanes 11 and 12, template-free control reactions. The size of the DNA markers is given in base pairs (bp).

Figure 18:
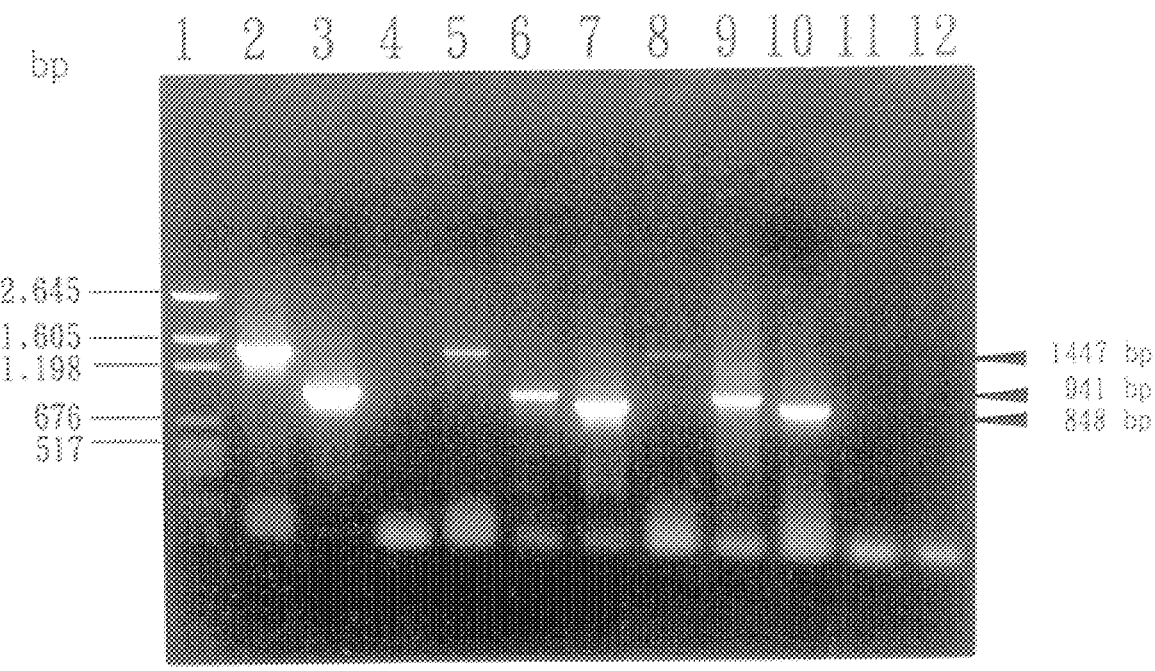

FIG. 18 shows the PCR amplification of WSBV and shrimp DNA specific fragments using DNA templates prepared from *Penaeus monodon* experimentally infected with WSBV. The primers 146F1 and 146 R1 which yield a 1447-bp PCR product were used for the reaction. The PCR products were analyzed on a 1% agarose gel. Lane 1, pGEN DNA size marker; lanes 2–4, DNA extracts from 3 experimentally infected *P. monodon*; lanes 5–7, DNA extracts from healthy *P. monodon* of control group. The size of DNA markers is indicated in base pairs (bp).

Figure 19:
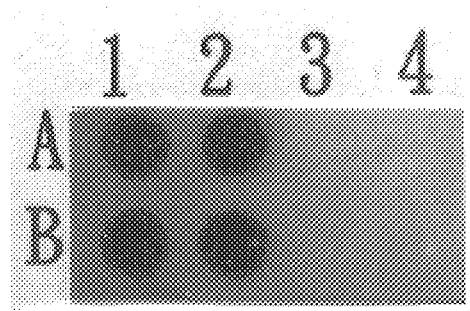

FIG. 19 is a Dot hybridization of DNAs extracted from WSBV infected or healthy *Penaeus monodon* with DIG-labeled 1447-kbp PCR product. The DNAs from 2 WSBV infected shrimp (1 and 2) and 2 healthy shrimp (3 and 4) were blotted in duplicate (A and B) onto the Hybond-N paper and probed with DIG-labeled 1447-bp PCR product. The probe hybridized with the DNAs from the infected shrimp but not with the DNAs from the healthy shrimp.

FIG. 20A and 20B are a Southern hybridization of WSBV DNAs from the diseased *P. monodon* or *P. japonicus* with DIG-labeled 1447-bp PCR product SalI digested WSBV DNAs from *P. monodon* and *P. japonicus* were blotted onto the Hybond-N paper and probed with DIG-labeled 1447-bp PCR product. The probe hybridized with a 1461-bp fragment of SalI digested WSBV DNA from either shrimp source with equal visual intensity showing their close relatedness. A: ethidium bromide-stained 0.8% agarose gel; B: the autoradiograph of the Southern blot of gel (A). Lane 1, PGEN DNA size marker; lane 2, genomic DNA SalI fragments of WSBV purified from *P. monodon*; lane 3 genomic DNA SalI fragments of WSBV purified from *P. japonicus.*

Figure 21:
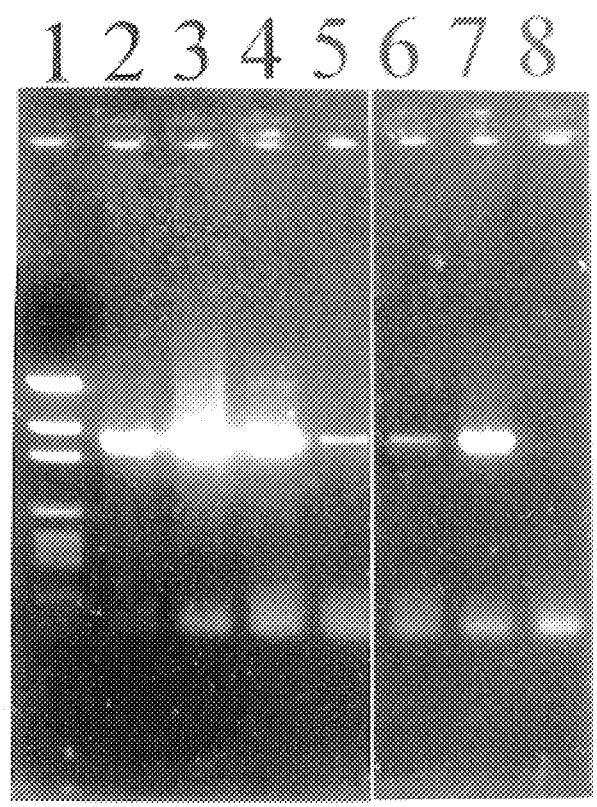

FIG. 21 shows the PCR amplication of WSBV DNA specific fragments using primer set 146F1/146F2 and DNA template prepared from arthropods collected from epizootic areas. Lane 1: PGEN marker; lane 2: *P. monodon;* lane 3: *P. japonica;* lane 4: crab; lane 5: copepoda; lane 6: insect (Family: Ephydridae); lane 7: positive control, DNA from known diseased shrimp; and lane 8: negative control, sample without addition of template.

DETAILED DESCRIPTION OF THE INVENTION

Outbreak of a disease causing serious financial losses among populations of cultured penaeid shrimps, including

*Penaeus monodon*, *P. japonicus* and *P. penicillatus* in Taiwan is characterized by obvious white spot on the carapace, appendages and the inside surface of the body. In order to identify the causative agent of white spot syndrome in penaeid shrimps, electron microscope observations of diseased shrimps were conducted. Healthy juvenile kuruma shrimps (*P. japonicus*) were exposed by immersion to epidermal filtrate from diseased *P. japonicus* and *P. monodon* which exhibited marked white spot signs. Challenge tests used this filtrate on different sized kuruma shrimps.

A non-occluded rod-shaped virus particle was found by electron microscopy in the epidermis of both spontaneously and experimentally infected kuruma shrimps. Virions were enveloped, 330±20nm in length and 87±7nm in diameter. These experimentally infected shrimps resembled the spontaneously affected ones. Direct inoculation of this virus-containing filtrate into fish cell lines showed no cytopathic effect. Cumulative mortalities reached 100% within 5–7 days and were significantly affected by catching and temperature stress.

The close resemblance in external signs and virus morphology between spontaneously diseased and experimentally infected shrimps indicated that the rod-shaped virus may be the main causative agent of the disease in Taiwan characterized by white spot syndrome. For this reason, this viral disease was proposed the name of "White Spot Syndrome" (W.S.S.). Further studies on the causative agent of W.S.S. (White Spot Syndrome associated Virus) isolated from *Penaeus monodon* in order to know its taxonomic position.

The causative viral agent was purified from diseased shrimp, *Penaeus monodon*, with white spot syndrome. Negatively stained preparations show that the virus is pleiomorphic. It is fusiform or rod-shaped. In negatively stained preparations, the virion measures 70 to 150 nm at its broadest point and is 250 to 380 nm long. In some virions, a tail-like projection extends from one end. The capsid is apparently composed of rings of subunits in a stacked series. The rings align perpendicularly to the longitudinal axis of the capsid. The genome of the virus is a double-stranded DNA molecule which produces at least 22 HindIII fragments. The full length of the DNA is estimated to be longer than 150 kbp. Based on the morphological characteristics and genomic structures of the virus, it is confirmed that white spot syndrome associated virus (WSSV) is a member of genus NOB (Non-Occluded Baculovirus) of the subfamily Nudibaculovirinae of Baculoviridae and the present isolate is designated as PmNOBIII, and as WSBV (Baculovirus associated with White Spot syndrome) to indicate PmNOBIII related agents.

The WSBV may be closely related to hypodermal and hematopoietic necrosis baculovirus (HHNBV) reported as the pathogen of the explosive epidemic disease of prawn (EEDS) in China in 1993–1994 (Cai et al., J. Fish. China, 19: 112–117, 1995) and systematic ectodermal and mesodermal baculovirus (SEMBV) of the black tiger prawn *Penaeus monodon* in Thailand (Wang et al., Dis. aquat. Org., in press, 1995; Wongteerasupaya et al., Dis. aguat. Org., 21: 69–77, 1995).

The principal clinical sign of this new viral disease is the presence of white spots on the exoskeleton and epidermis of the diseased shrimp with varied sizes from barely visible to 3 mm in diameter. Histopathological study demonstrates that WSBV attacks most frequently the cuticular epidermis, as evidenced by the presence in these tissues of the degenerated cells characterized by hypertrophied nuclei (Momoyama et al., Fish Pathol., 29: 141–148, 1994, Chou et al., Dis. aquat. Org., in press, 1995; C. H. Wang et al., 1995). Thus, the white spot syndrome in penaeid shrimp associated with non-occluded baculovirus can be said to be a well-defined disease and in the represent studies we used an isolate of WSBV from *P. monodon* as the starting material to develop a diagnostic tool for the detection of WSBV in shrimps.

To develop a diagnostic tool for the detection of WSBV and related agent infection in shrimps, the virions were purified from black tiger shrimp *Penaeus monodon* infected with WSBV. Extraction of viral genomic DNA from purified virions was done by treating the virions with proteinase K and cetyltrimethyl-ammonium bromide (CTAB) followed by phenol-chloroform extraction and ethanol precipitation. A qualitative assessment was performed using polymerase chain reaction (PCR) on the viral DNA and primers specific to shrimp genomic DNA for monitoring shrimp DNA contamination in the viral genomic DNA preparations. A WSBV genomic DNA library was constructed and based upon the sequence of the cloned WSBV DNA fragment, a WSBV specific primer set for PCR to detect the WSBV infection in penaeid shrimps has been designed.

Samples which contained WSBV DNA yielded an evident amplification product showing the expected mobility of a 1447-bp DNA fragment, whereas the nucleic acids extracted from tissue samples from clinically healthy shrimp showed no such DNA fragment, thereby confirming the specificity of the WSBV DNA specific primers designed in the present invention. By PCR with the WSBV specific primer set, it has been demonstrated that the causative agents of white spot syndrome in different shrimp species are in fact closely related. Other host organisms, including copepoda, crabs and insects are also tested for the presence of this new causative agent and the currently collected experimental data are positive. The results of this invention provide an effective diagnostic tool for screening shrimp for WSBV infections, which may be extremely important in preventing the further spread of this viral disease.

Materials and Methods

Shrimp. The healthy kuruma shrimps used for challenge tests were obtained from a hatchery and a shrimp farm in southern Taiwan where no viral disease had been reported. All of the kuruma shrimps were maintained at a temperature of 25–28° C. aquaria with aeration and fed on artificial, commercially obtained shrimp food twice daily. Diseased shrimps of *P. japonicus* were collected from a culture farm in northern Taiwan, while samples of moribund penaeid shrimp, *P. monodon* (average weight: 30 g) were collected from shrimp farms located in southern Taiwan in November 1994. The samples were examined by gross anatomy, light and electron microscopes for the confirmation of the disease using the methodologies as described hereunder. For light microscopy, both normal kuruma shrimps and individuals displaying marked white spot signs were preserved in Davison's fixative (Bell & Lightner 1988). After 48h in Davison's fixative, specimens were transferred to 50% ethanol, and then processed routinely for histology to 5 μm paraffin wax sections, and stained routinely with hematoxylin and eosin (H & E). For transmission electron macroscopy, sample of epidermis covering the gill chamber underneath the carapace was removed from naturally and experimentally infected live kuruma shrimps, and immediately prefixed in 2.5% glutaraldehyde in 0.1M cold phosphate buffer solution (PBS, pH 7.4) for 2hr at 4° C. Subsequently, samples were washed several times in cold PBS, and then postfixed in 1% osmium tetroxide for 3 hr at 4° C. The samples were dehydrated and embedded in Spurr's resin.

Ultrathin sections were prepared on a Richert-jung Ultracut E Ultrotome, and stained with uranyl acetate and lead citrate. The sections were observed with a HITACHI H-600 transmission electron microscope.

Challenge test. The epidermis from infected *P. monodon*

Challenge test. The epidermis from infected *P. monodon* was removed and homogenized in brackish water at 4° C. in the ratio of 1:9. After being centrifuged at 8510×g (Sigma 2K15 rotor 12141) for 5 min, the supernatant was filtered through a 0.45 μm membrane. The filtrate was centrifuged at 14,549×g (Sigma 2K15 rotor 12139) for 1.5 hr and the resulting pellet was resuspended in sterilized brackish water before being applied with negative staining. For negative staining, one drop of suspension was mixed with four drops of the mixture of 0.1% bovine serum albumin and 2% phosphotungstic acid (1:2, pH 7.0). The mixture was placed on a 300 mesh grid for 30–60 sec and excess suspension was removed with filter paper. The preparation was allowed to dry before being examined. Result was observed under a HITACHI H-600 transmission electron microscope.

Crytopathology assay. EPC (epithelioma papulosum cyprini), CHSE-214 (chinook salmon embryo), FHM (fathead minnow) and SSE-5 (sockeye salmon embryo) cells were seeded in 24-well microplates. A filtrate was made from the epidermis of the diseased shrimps and was diluted from 1/20 to 1/12500 in 5-fold dilutions. Diluted solutions were inoculated into the four fish cell lines and these cells were observed over 2 weeks at an incubation temperature of 20° C.

An infection trial was performed using the filtrate of the epidermis from live or frozen naturally infected *P. japonicus* and *P. monodon*. The filtrate was diluted 500- 750 times in brackish water in order to be used as a waterborne inoculum. Two replicates of thirty-five one-month-old juvenile kuruma shrimps (mean weight 0.08g) were immersed in these diluted filtrates for 2h. Two other populations were similarly exposed, either to the filtrate from healthy *P. monodon* epidermis or to Grace's insect medium. These served as controls. After inoculation, shrimps were kept in glass aquaria with aeration. Water temperature and salinity were 25–28° C. and 25–30 ppt, respectively, throughout the experiment. The mortality was observed daily and the moribund shrimps were collected and examined by transmission electron microscopy.

Purification, Genomic Structure and Taxonomic Position of WSBV

The purification of the virions of WSSV from *P. monodon* shrimp was carried out as follows. The shrimps were first rinsed with cold 1×TE buffer (10 mM Tris-HCl, 1 mM EDTA, pH 7.6). The exoskeleton with underlying epidermis taken from 1 to 5 live or frozen shrimp was extracted with 20 ml cold extraction buffer (20 mM HEPES, 0.4 N NaCl, 1 mM EDTA, 1 mM EGTA, 1 mM DTT, 2.5 mM phenylmethylsulfonyl fluoride, 1 μg/ml leupeptin, 1.6 ug/ml pepstatin, 2 μg/ml aprotinin, 1 μg/ml bestatin), and then purified by centrifugation on linear 35 to 65% (W/W) sucrose gradient at 74,700×g (Hitachi SRP 28SA rotor at 24,000 rpm) for 60 min. The visible viral band in the centrifugation at 74,700 ×g at 4° C. for 30 min. The pellet was washed twice with cold 1×TE buffer, resuspended with 300–500 ml cold 1×TE buffer depending on the size of the pellet, and immediately used for viral DNA extraction. A small volume of purified virus suspensions was negatively stained with 2% phosphotungstic acid (PTA) at pH 7 for the ultrastructural studies of the virions.

The extraction of viral genomic DNA from gradient purified virions was performed by proteinase K and N-cetyl N,N,N-trimethylammonium bromide (CTAB) treatments followed by phenol-chloroform extraction and ethanol precipitation (K. Wilson (1994), Preparation of genomic DNA from bacteria. Miniprep of bacterial genomic DNA. in Ausubel, F. M. et al. (eds.) Current Protocols in Molecular Biology, Vol.1. Greene Pub. Assoc. and Wiley-Interscience, NY, p. 2.4.1-2.4.5).

The estimation of the viral genome size was done by restriction endonuclease analysis. Viral DNAs were digested with HindIII, SalI and XhoI restriction endonucleases (Boehringer Mannheim Company). Restriction fragments were separated by electrophoresis in 0.8% agarose gel (9cm×12cm), with Tris-acetate buffer (0.04 M Tris-acetate, 0.1 mM EDTA, pH 8.0) containing 0.5 μg/ml ethidium bromide. The 1-kilobase (kb) DNA ladder and lambda phage HindIII fragment marker (Life Technologies, Inc.) were used as the DNA size standard on the gel.

Development of Effective Diagnostic Tools

For the development of effective diagnostic tools, the construction of WSBV genomic library was conducted by cloning "super pure" WSBV genomic DNA extracted from purified virions. In addition, the amplification of selected DNA sequence by polymerase chain reaction (PCR) promises to be a powerful diagnostic tool for the identification of pathogens (Erlich et al., Nature 331: 461–462, 1988; Oste, C., Biotechniques 6: 162–167, 1988). Based upon the sequences of the cloned WSBV DNA fragments, a WSBV specific primer set for PCR has been designed.

I. WSBV genomic DNA library construction

A. Virus purification and extraction of viral DNA

The same batch of the frozen WSBV infected black tiger shrimp *Penaeus monodon* , as used for the taxonomic studies, was the source of the virus, and this strain of the WSBV is named as PmNOBIII (the third non-occluded baculovirus reported for *P. monodon*) according to the criteria set forth in Francki et al. (Arch. Virol., 2: 1–450, 1991). The purification of the virions was carried out as described in the previous paragraphs. The extraction of viral genomic DNA from purified virions was performed by treating the virions with proteinase K and N-cetyl N,N,N-trimethylammonium bromide (CTAB) followed by phenol-chloroform extraction and ethanol precipitation (Wilson (1994), supra). Briefly, the gradient-purified virions were incubated in TE buffer (10 mM Tris-HCl, 1 mM EDTA, pH 7.6) containing 100 mM KCl, 1% SLS (N-lauryl sarcosine) and 0.2 mg/ml proteinase K at 65° C. for 3 hr. After incubation, 5 M NaCl was added to adjust the NaCl concentration of the DNA solution to 0.7 M. Next, 1/10 vol. CTAB/NaCl (10% CTAB in 0.7 M NaCl) was added slowly and mixed thoroughly before incubation at 65° C. for 10 min.

Following two extractions with an approximately equal volume of chloroform/isoamyl alcohol and two extractions with an equal volume of phenol/chloroform/isoamyl alcohol, the DNA was precipitated with two volumes of absolute ethanol, and washed with cold 70% ethanol. The dried DNA pellet was dissolved in a suitable amount of 0.1×TE buffer at 65° C. for 30 min, and then stored at 4° C. until use.

B. Preparation of shrimp DNA for PCR as a control

The primers specific to shrimp genomic DNA for PCR were used to monitor shrimp DNA contamination in the WSBV genomic DNA preparations. For this purpose, two primers were designed from the highly conserved regions of 18S rRNA sequence of decapods, based on published sequences (Kim & Abele, J. Crust. Biol., 10, 1–13, 1990), a computerized data file (GenBank, National Institute of Health, MD, U.S.A.) and the sequence alignment analysis using PC/GENE program (Intelligenetics, Inc.). By pairing the forward primer 143F (5'- TGC CTT ATC AGC TNT CGA TTG TAG-3'(SEQ. ID. NO: 13), where N represents G, A, T or C) with a reverse primer 145R (5'-TTC AGN TTT GCA ACC ATA CTT CCC-3'(SEQ. ID. NO: 14), the shrimp DNA is expected to yield a PCR product of 848 bp corresponding to nucleotide sequences 352 to 1200 of 18S rRNA of P. aztecus.

The genomic DNAs extracted from the muscle of healthy P. monodon or P. japonicus were used as positive control for PCR. The deproteinized genomic DNA of the shrimp was prepared according to the method for preparation of genomic DNA from mammalian tissue (Strauss, WM (1994) Preparation of genomic DNA from mammalian tissue. In Ausubel FM, Brent R, Kingston RE, Moore DD, Seidman JG, Smith JA, Struhl K (Eds) Current Protocols in Molecular Biology, Vol.1. Greene Publishing Associates, Inc. and John Wiley and Sons, Inc., New York, p. 2.2.1–2.2.3). Briefly, 200 mg muscle tissue excised from the abdomen of the shrimp was rapidly frozen in liquid nitrogen and crushed to a fine powder. The processed tissue was placed in 2.4 ml digestion buffer (100 mM NaCl, 10 mM Tris-HCl, pH 8, 25 mM EDTA, pH 8, 0.5% sodium dodecyl sulfate, 0.1 mg/ml proteinase K) and incubated at 65° C. for 12 to 18 hr. The digest was deproteinized by successive phenol/chloroform/isoamyl alcohol extractions, recovered by ethanol precipitation, and dried and resuspended in 0.1×TE buffer at 65° C. for 30 min, and then stored at 4° C. until use for PCR.

C. WSBV genomic DNA library construction

Two WSBV genomic libraries, PmNOBIII SalI (pms) and PmNOBIII HindIII (pmh) were constructed as set forth below. The WSBV genomic DNA without shrimp DNA contamination was digested with SalI or HindIII restriction endonuclease (BRL, Life Technologies Inc.) at 37° C. for 3 hr in order to obtain DNA fragments, and the fragments were then ligated into SalI or HindIII cleaved pUC 19 plasmid vector in the presence of T4 DNA ligase at 16° C. overnight. The competent Escherichia coli DH 5α a cells were transformed with the resulting plasmids and plated on ampicillin/isopropyl-β-D-thiogalactopyranoside (IPTG)/5-bromo-4-chloro-3-indolyl-β-D-galactopyranoside (X-gal) agar plates. After using miniprep method to screen the white ampicillin-resistant transformants for the presence of the appropriate recombinant plasmids, both strands of the plasmid inserts were sequenced with double-stranded DNA templates using a Sequenase kit (United States Biochemical Corp.) with M13/pUC Sequencing Primers (GIBCO BRL Life Technologies Inc.), and subsequently, specific internal primers. Recombinant plasmids were isolated from transformants and screened for the presence of the insert by SalI or HindIII digestion. The size of the inserts were listed in Table 1.

II. Amplification of WSBV DNA fragment from DNA extracted from purified WSBV virions Oligonucleotide primers (146F and 146R) are used for the amplification of WSBV DNA fragments. Primers 146F and 146R are designed on the basis of the DNA sequence of a cloned WSBV 1461-bp SalI DNA fragment in recombinant plasmid pms146 and there have been established 6 primer sets as shown in FIG. 15D. The primer set of 146R1 and 146F1 have the following nucleotide sequences: 146R1, 5'-TAA TGC GGG TGT AAT GTT CTT ACG A-3'(SEQ. ID. NO: 4)(SEQ. ID. NO: 3); 146F1, 5'-ACT ACT AAC TTC AGC CTA TCT AG-3'(SEQ. ID. NO: 3)(SEQ. ID. NO: 2). With this primer set, a 1447-bp fragment is expected to be amplified from WSBV genomic DNA. The internal primer set, 146R2, 5'-TAC GGC AGC TGC TGC ACC TTG T-3'(SEQ. ID. NO: 6)(SEQ. ID. NO: 5), and 146F2, 5'-GTA ACT GCC CCT TCC ATC TCC A-3'(SEQ. ID. NO: 5)(SEQ. ID. NO: 4) are used to confirm that the amplified fragment is indeed from the WSBV 941-bp SalI DNA fragment.

The deproteinized DNA samples extracted from purified WSBV virions and from the muscle of the healthy shrimp were used as DNA templates for the evaluation of the specificity of the primers by PCR.

III. Amplification of WSBV DNA fragment from DNA extracted from tissues of shrimp naturally and experimentally infected with WSBV The diseased shrimps consisted of shrimp naturally and experimentally infected with WSBV. For experimental infection, the healthy shrimp (average body weight: 0.5 gm) were infected with WSBV using the method described in the preceding paragraphs. Five days after infection, the DNAs were extracted from three experimentally infected shrimp and three healthy shrimp and checked by PCR with the use of WSBV specific primers (146F1 and 146R1) and shrimp DNA specific primers (143F and 145R).

IV. PCR amplification and analysis of products

The deproteinized DNA samples used for amplification totaled 0.1–0.3 mg in a 100-ml reaction mixture containing 10 mM Tris-HCl, pH 9 at 25° C., 50 mM KCl, 1.5 mM MgCl2, 0.1% Triton X-100, 200 μM each of dNTP, 100 pmol each of primer, 2.5 units of Taq DNA Polymerase (Promega). The amplification was performed in a AG-9600 Thermal Station (Biotronics Corp.) for one cycle of 94° C. for 4 min, 55° C. for 1 min, 72° C. for 3 min; 39 cycles of 94° C. for 1 min, 55° C. for 1 min, 72° C. for 3 min, plus a final 5 min extension at 72° C. after 40 cycles. Control reactions containing no template DNAs were run for all PCR reactions. In some PCR reactions, controls also consisted of reaction mixtures with DNA extracts from healthy shrimp. The PCR products were analyzed in 1% agarose gels containing ethidium bromide at a concentration of 0.5 μg/ml, and visualized under an ultraviolet transillumination.

V. Dot hybridization of DNAs extracted from WSBV infected or healthy P. monodon with DIG-labeled 1447-bp PCR product The DNAs extracted from WSBV infected or healthy P. monodon were spotted onto Hybond-N paper (Amersham) using a 96-well dot-blot vacuum filtration manifold apparatus (Schleicher and Schuell, Inc.). The blots were air dried and denatured in 1.5 M NaCl, 0.5 N NaOH for 10 min, and then neutralized in 1.5 M NaCl, 1 M Tris, pH 7.4 for 10 min. The blots were used for hybridization with a DIG-labeled 1447-bp PCR product following the standard molecular cloning techniques (Sambrook J, Fritsch EF, Maniatis T (1989,) Molecular Cloning: A Laboratory Manual, 2nd. Cold Spring Harbor Laboratory Press, Cold Spring Harbor, N.Y.). The dot blot was hybridized at 37° C. for 16 hr with the DIG-labeled probe, after prehybridization at 37° C. for 12 hr in 50% formamide, 5×SSC, 1 mM EDTA, 50 mM Tris (pH 8), 5×Denhardt's reagent (0.1% Ficoll-400, 0.1% polyvinyl pyrrolidone, 0.1% BSA). The 1447-bp PCR product was used as a template to prepare probe using the random primer method (Boehringer Mannheim). After hybridization, the detection of the DIG-labeled nucleotides in blots was accomplished with a chemiluminescent reaction by using the DIG Luminescent Detection Kit (Boehringer Mannheim). The blot was exposed to Kodak XAR-5 film at 37° C. for 15–30 min to record the chemiluminescent signal.

VI. Southern hybridization of WSBV DNAs from the diseased P. inonodon or Py. japonicus with DIG-labeled 1447-bp PCR product Southern blot hybridization was performed to localized the 1447-bp PCR product within the genomic DNA of WSBV purified from the diseased *P. monodon* or *P. japonicus* with white spot syndrome. For this purpose, 200 ng genomic DNA of WSBV isolated from the diseased shrimp was digested with SalI, and then electrophoretically separated in 0.8% agarose gel. After acid (0.25 N HCl) depurination and alkali (1.5 M NaCl-0.5 N NaOH) denaturation of the DNA, the gel was neutralized with 1 M Tris (pH 7.4) and 1.5 M NaCl, and subsequently transferred to a Hybond-N nylon membrane using a vacuum transfer unit (Hoefer TE 80) for 60 min. The 20×SSC (3 M NaCl, 1.5 M Sodium Citrate) was used as transfer buffer (Sambrook et al. (1989), supra). The blot was used for hybridization with a DIG-labeled 1447-bp PCR product.

VII. Detection of WSBV in Arthropods Collected from Epizootic Areas

The DNA templates prepared from arthropods collected from epizootic areas were used for PCR with 146R1 and 146F1 primers for the detection of WSBV in the tested organisms.

RESULTS

A. Histopathological studies:

Outbreaks of W.S.S. amongst penaeid shrimps is evidently not a confined, local problem anymore. It has already brought the cultured shrimp industry in Asia to a critical condition. In order to classify the causative virus more clearly and develop a quick diagnostic method, further studies on the physicochemical characterization of this agent is conducted.

Figure 1:
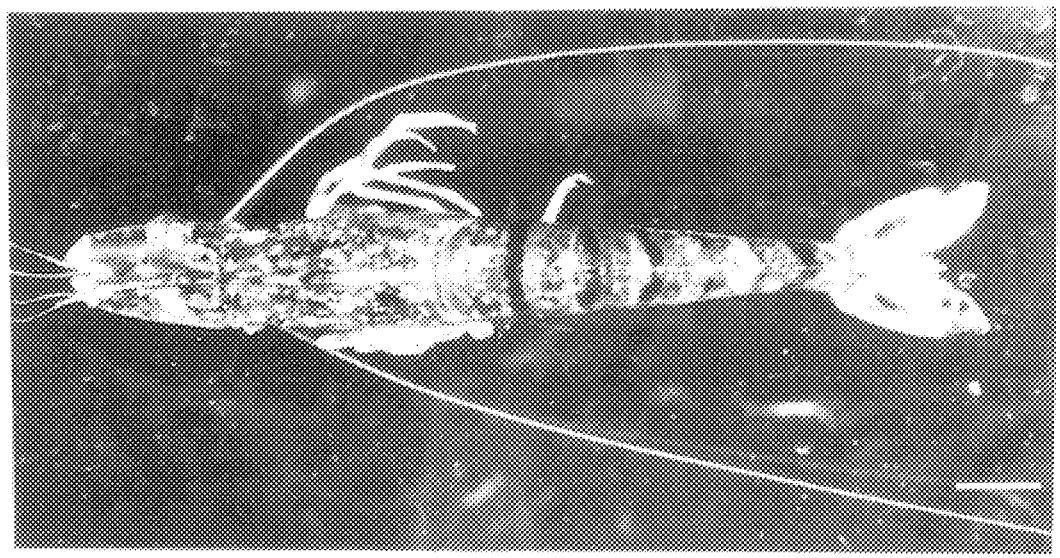
FIG. 1 is a photograph of *Penaeus monodon* with white spot syndrome showing the white spots from barely visible to 3 mm in diameter. Bar: 1 cm.
Figure 2:
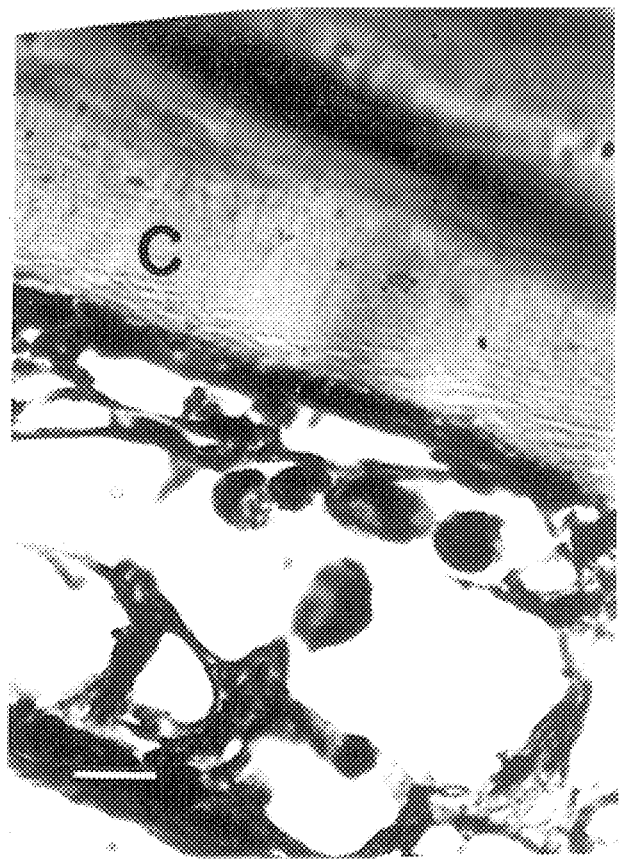
FIG. 2 is a light micrograph of cuticular epidermis under the cephalothorax exoskeleton (C) from *Penaeus monodon* with white spot syndrome showing basophilic inclusions in hypertrophied nuclei of degenerated cells (arrows). Bar: 10 mm.

The main clinical signs of the disease in *Penaeus monodon* were the white spots on the exoskeleton (FIG. 1). The white spots were particularly obvious on the carapace removed from the diseased shrimp, and were readily observed even on the carapaces from lightly infected animals. Histopathological study demonstrates that epidermis of the diseased shrimp was attacked by viral agent evidenced by the presence in this tissue of the degenerated cells characterized by hypertrophied nuclei with inclusions (FIG. 2).

Figure 3:
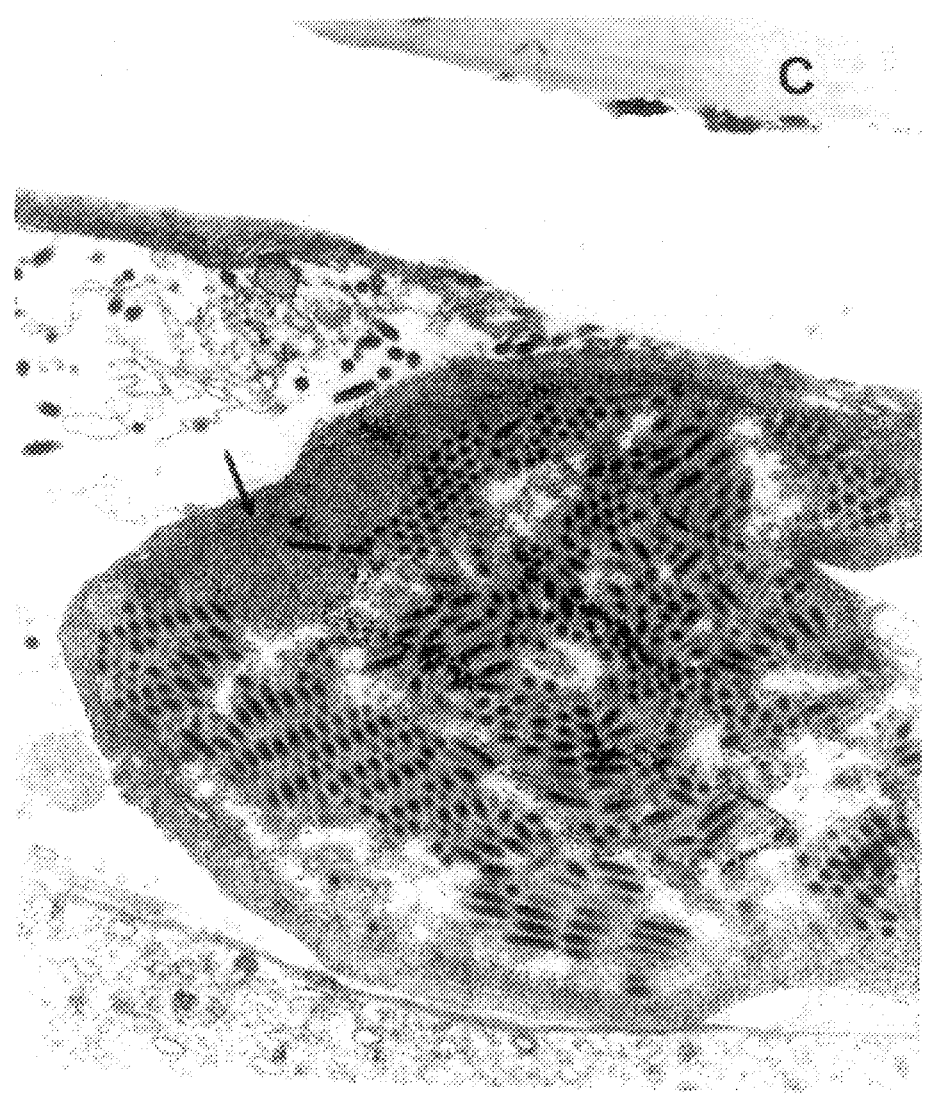
FIG. 3 is a transmission electron micrograph of thin-sectioned infected tissues underneath the cephalothoracic exoskeletal cuticle (C) from *Penaeus monodon* with white spot syndrome showing virus particles in the necrotic area and in a hypertrophied nucleus (Arrow). Bar: 0.5. mm.
Figure 4:
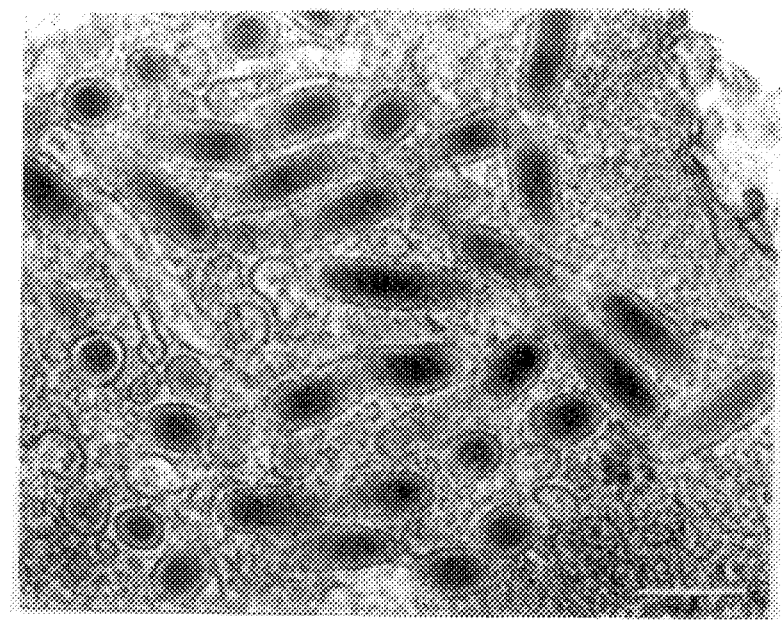
FIG. 4 shows rod-shaped viral particles in the epidermis of experimentally infected *P. japonicus* with the filtrate obtained from diseased *P. monodon*) Scale bar =200 nm.

Ultrathin sections of the underlying epidermis of the cuticle from shrimp with white spot syndrome viewed under the electron microscope revealed numerous non-occluded baculo-like virus particles in the necrotic areas. The hypertrophied nuclei filled with virions were also readily seen (FIG. 3). The virus particles were 330±20 nm in length and 87±7 nm in diameter (n=30). The electron-dense central core of the virus particle is nucleocapsid, approximately 220×70 nm in size. No difference in virion morphology between spontaneously diseased and experimentally infected shrimp was recognized (FIG. 4).

B. Negative staining and cytotoxicity assay of the filtrate for challenge test

The result of negative staining of the pellet from the filtrate of diseased *P. monodon* epidermis is shown in FIG. 5. Virus particles with rod-shape morphology can be seen. These are similar to the virus particles observed in ultrathin sections of spontaneously diseased shrimps. No bacteria were observed.

Cytopathic effect (CPE) was not found in any of the four tested fish cell lines; the filtrate which was used as waterborne inoculum had no cytotoxicity.

C. Challenge test

Healthy shrimps were exposed to epidermal filtrate from diseased *P. japonicus* and *P. monodon* which exhibited marked white spot symptoms. These experimentally infected shrimps resembled the spontaneously affected ones (FIG. 6) and cumulative mortalities reached 100% within 5–7 days (FIG. 7), while no shrimp died in the control groups.

Further, the inoculum was highly pathogenic to the smallest shrimps tested (mean weight of 0.08 g) and all these shrimps died within 5 days; only 35% cumulative mortality was found in the 0.16 g-sized shrimp group after 7 days although mortality reached 100% in 12 days; and 10% mortality was observed in the group of largest shrimp (mean weight of 0.26 g) within 2 weeks. No shrimp died in the control groups.

D. Purification, Genomic Structure and Taxonomic Position of WSBV

The purified virions were fusiform or rod-shaped with bluntly rounded ends. In negatively stained preparations, the virion was 70 to 150 nm at its broadest point, and was 250 to 380 nm long, which is usually 10% larger than in ultrathin sections. In some virions, a tail-like projection extending from one end was observed (FIG. 8). The non-enveloped nucleocapsids were normally 58 to 67 nm in diameter and 330 to 350 nm long. The capsid components formed parallel cross-striations (FIG. 9). Thus, the capsid seemed to be composed of rings of subunits in a stacked series. The thickness of the rings (20 nm) was very constant and the rings were perpendicular to the longitudinal axis of the capsid. In term of virus morphology, WSSV resembles SEMBV (Systemic Ectodermal and Mesodermal Baculovirus) and differs from BMN (Baculoviral Mid-gut Gland Necrosis Virus) and PmSNPV (*Penaeus monodon* Single Nucleocapsid Nuclear Polyhedrosis virus=MBV) (Mari et al., Dis. aquat. Org. 16: 207–215, 1993; Sano et al., Helgolander Meeresunters. 37: 255–264, 1984; Wongteerasupaya et al., Dis. aquat. Org. 21: 69–77, 1995). However, the main clinical sign of white spot caused by WSSV was not described in the SEMBV infected shrimp. To date, it is difficult to guess the relatedness between WSSV and SEMBV.

A single DNA molecule was extracted from purified virions of WSSV (FIG. 10). The genomic DNA of WSBV digested with HindIII, SalI and XhoI restriction endonucleases was shown in FIG. 11. The genomic DNA of WSSV digested with HindIII restriction endonuclease produced, in the agarose gel, at least 22 fragments of approximate sizes: 19.4, 16.9, 14.9, 12.5, 10.0, 9.6, 8.4, 8.0, 7.3., 6.1, 5.5, 4.8, 4.3, 3.9, 3.6, 3.3, 3.0, 2.5, 2.0, 1.6, 1.4, and 1.1 kbp, respectively. The fragments smaller than 1 kbp have run over the gel if they exist. The length of WSSV DNA was estimated to be longer than 150 kbp, which falls within the size range of 90–230 kbp found in insect baculoviruses (Francki et al., Arch. Virol., suppl. 2: 1–450, 1991).

Based on the morphological characteristics and genomic structure, WSSV is classified as the genus Non-Occluded Baculovirus (NOB) of the subfamily Nudibaculovirinae of Baculoviridae (Francki et al. (1991), supra) and the isolate was named PmNOBIII, as the third non-occluded baculovirus reported for *P. monodon* (D.V. Lightner, Boca Raton, p. 393–486, 1993; Wongteerasupaya et al (1995), supra). It is also proposed to use WSBV (Baculovirus associated with White-spot Syndrome) to indicate the PmNOBIII related agents.

E. Development of Effective Diagnostic Tools for WSBV Infection

I. WSBV genomic DNA library construction a) Virus purification and extraction of viral DNA Typical rod-shaped virions of WSBV were readily observed after concentration and purification by sucrose gradient centrifugation. These virions were used to extract the viral DNA.

The amplification of shrimp DNA using PCR and primers specific to 18S rRNA reliably resulted in a predicted 848-bp DNA fragment (FIG. 12). This provided a simple and highly sensitive method for detecting small amounts of shrimp DNA and was subsequently used to monitor shrimp DNA contamination in WSBV genomic DNA preparations for library construction. The PCR analysis shown in FIG. 13 indicates that host DNA contamination was detected in most WSBV genomic DNA preparations. However, a few samples of WSBV genomic DNA extracted from purified virion preparations were virtually free of contaminating host DNA. An example is shown in FIG. 13, lane 3.

b) Genomic DNA library construction

Two WSBV genomic libraries, PmNOBIII SalI (pms) and PmNOBIII HindIII (pmh) were constructed with use of SalI or HindIII restriction endonuclease (BRL, Life Technologies Inc.) and pUC 19 plasmid vector.

For example, the SalI digested WSBV DNA was checked by electrophoresing a 5-ml aliquot in a 0.8% agarose gel containing ethidium bromide. The WSBV genomic DNA was completely digested with SalI restriction endonuclease (FIG. 14). From the same batch of digested DNA, a 20-ml aliquot was used for library construction.

Recombinant plasmids isolated from transformants were screened by SalI or HindIII digestion, among which 592 clones (pms1-pms592) from pms library and 410 clones (pmh1-pmh245 and pmh419-pmh584) from pmh library were screened for the presence of the insert by SalI or HindIII digestion. The size of the inserts varied from 15kbp to less than 100bp as shown in Table 1. These libraries provide an abundant supply of WSBV DNA, enabling further study of the molecular biology of the virus and development of nucleic acid and immunological diagnostic kits.

II. Amplification of WSBV DNA fragment from deproteinized DNA extracted from purified virions On the basis of the obtained DNA sequences (data not shown) of WSBV SalI DNA fragments, several primer sets were designed and evaluated by PCR for their ability to identify the WSBV in infected tissues.

FIG. 15A displays a diagram of the SalI-1461 bp DNA fragment cloned in plasmid pms146 and FIG. 15B shows the locations of the primers, which are used for PCR amplication, in the SalI-1461 bp DNA fragment. The 146F1 and 146R1 prime the amplification of a 1447-bp fragment, while 146F2 and 146R2 prime the amplification of a 941-bp fragment. The positions of two EcoRI sites in SalI 1461 bp DNA fragment are also indicated. FIG. 15C shows the detailed nucleotide sequence of the SalI-1461 bp fragment, in which the locations of the two primer sets 146F1/146R1 and 146F2/146R2 and the two EcoRI sites are also indicated. FIG. 15D shows the nucleotide sequences of six primer sets developed from the SalI-1461 bp fragment. Among them, the primer set 146F1/146R1 gave a consistent and an efficient amplification of WSBV DNA but not of shrimp DNA. This primer set was then chosen for subsequent parts of this study.

FIG. 16 shows the results of amplification using purified WSBV genomic DNA as PCR template, and the primer sets either specific to WSBV DNA or to shrimp DNA. The reactions analyzed in FIG. 16, lanes 2, 5 and 8 represent amplification using WSBV DNA primer set 146F1-146R1 and three independent WSBV DNA preparations, and the results demonstrate the presence of a relatively large amount of WSBV genomic DNA in the three tested samples, as evidenced by an intense 1447-bp PCR product in these lanes. At least one of the WSBV DNA preparations is free from shrimp DNA contamination, as evidenced by the absence of detectable PCR product of shrimp DNA in FIG. 16, lane 6. The WSBV primer set 146F1/146R1 and shrimp DNA primer set 143F/145R were used simultaneously in a reaction mixture for demonstrating approximately the proportion of WSBV DNA in template DNAs.

The data presented in FIG. 16 demonstrate that WSBV specific DNA fragment was detected as a major band in three independent WSBV preparations (lanes 4, 7 and 10) while the shrimp DNA was detected in two of three WSBV DNA preparations (lanes 3 and 10). Thus template DNAs contained varying proportions of shrimp DNA and WSBV DNA. It is also clear that in spite of contamination with shrimp DNA, a large proportion of the DNAs extracted from WSBV virions purified by sucrose gradient centrifugation is WSBV DNA. Meanwhile, reaction mixtures with total nucleic acid extracted from tissues from clinically healthy shrimp and WSBV DNA specific primer set 146F1/146R1 were consistently negative (FIG. 16, lane 11) thus demonstrating the specificity of this primer set.

III. Amplification of WSBV DNA fragment from DNA extracted from the shrimp tissues naturally and experimentally infected with WSBV FIG. 17 shows the amplification results using plasmid pms146 DNA and the DNA extracted from the tissues of *P. monodon* and *P. japonicus* naturally infected with WSBV as DNA templates. The DNA templates were amplified using either the WSBV-specific primer set 146F1/146R1 or shrimp DNA-specific primer set 143F/145R. The 1447-bp PCR product, comigrating with DNA amplified from pure plasmid pms146 DNA, demonstrates the presence of WSBV DNA in the total nucleic acid extracted from all the naturally infected shrimp. Examples are shown in FIG. 17, lanes 2, 5 and 8.

Using the internal primer set 146F2/146R2, 10 µl of these products were reamplified to yield a PCR product with the expected size of 941 bp (FIG. 16, lanes 3, 6 and 9). The results confirm the identity between amplification product and template. Shrimp DNA was amplified very efficiently using shrimp DNA specific primer set 143F/145R as shown in FIG. 17, lanes 7 and 10. The results presented in FIG. 17, lanes 5 to 10 demonstrate that WSBV DNA could be detected with the use of WSBV DNA specific primer sets 146F1/146R1 and 146F2/146R2 in the presence of a large excess of shrimp genomic DNA.

FIG. 18 shows the amplication result using DNA extracted from tissues of *P. monodon* experimentally infected with WSBV as DNA templates for PCR using primer set 146F1/146R1. Amplification of the expected 1447-bp fragment is evident for all the experimentally infected shrimp. No amplification product at 1447 bp was present for healthy shrimp from control group.

IV. Dot hybridization of DNAs extracted from WSBV infected or healthy *P. monodon* with DIG-labeled 1447-bp PCR product The results of dot hybridization demonstrate that the PCR product hybridized with DNAs extracted from WSBV infected shrimp, but did not hybridize with DNAs extracted from healthy shrimp. (FIG. 19). The results demonstrate the specificity of the 1447-bp PCR product.

V. Southern hybridization of WSBV DNAs from the diseased *P. monodon* or *P. japonicus* with DIG-labeled 1447-bp PCR product In order to localize the 1447-bp PCR product within the WSBV genomic DNA, Southern hybridization of WSBV genomic DNA SalI fragments was performed using DIG-labeled 1447-bp PCR product as a probe. The results demonstrate that 1447-bp PCR product hybridized specifically with a WSBV genomic DNA SalI fragment of 1461 bp (FIG.

20). Both 1461 bp SalI fragments of WSBV genomic DNAs prepared respectively from *P. monodon* and *P. japonicus* were found to be positive with the probe.

VI. Detection of WSBV in Arthropods Collected from Epizootic Areas

Among tested organisms, *P. monodon, P. japonicus,* crabs, copepoda and insect (Family: Ephydridae) gave WSBV positive results (FIG. 21).

DISCUSSION

The diseased shrimps have obvious white spots on the carapace, appendages and the inside surface of the body, and also display signs of lethargy and reddish coloration of the hepatopancreas. Vibriosis, virus infection, poor environmental management and nutrient imbalance have all been conjectured to be the possible cause for these outbreaks. Based on electron microscope observation, however, a rod-shaped virus ws considered to be the main causative agent. In the present study, the pathogenicity of a pathogenic virus from diseased *P. japonicus* and *P. monodon* with white spot syndrome was investigated. Close resemblance in white spot signs and virus morphology between spontaneously diseased and experimentally infected shrimps demonstrated that this virus is indeed the causative agent of the outbreak. The virus is highly pathogenic and constitutes a threat to shrimp. Information pilot studies in which diseased shrimps were fed to healthy specimens suggest that the virus may be transmitted orally as well as via water.

In addition to WSBV, a variety of baculoviruses has been reported to infect decapod crustaceans since the first report by Couch (Nature, 247 (5438): 229–231, 1974; J. Invertebr. Pathol., 24: 311–331, 1974) and some of them cause mass mortality of the diseased animals (Lightner & Redman, J. Invertebr. Pathol., 38: 299–302, 1981; Sano et al., Fish Pathol., 15: 185–191, 1981; Lester et al., Dis. aquat. Org., 3: 217–219, 1987; Johnson P. T., Dis. aquat. Org., 5: 111–122, 1988; Johnson & Lightner, Dis. aquat. Org., 5: 123–141, 1988; Bruce et al., J. Virol. mehods, 34: 245–254, 1991; Chang et al., Fish Pathol., 27 (3): 127–130, 1992; Chang et al., J. Invertebr. Pathol., 62: 116–120, 1993; Mari et al., Dis. aquat. Org., 16: 207–215, 1993, Wongteerasupaya et at., Dis. aquat. Org., 21: 69–77, 1995). These viruses are morphologically similar, and most researchers agree that the structure of the viral genome should become the much needed reference for determining the taxonomic position of crustacean baculoviruses. The development of rapid and reliable diagnostic tools using molecular approaches will be useful not only for the identification and comparative studies of the viruses but also for the screening of carriers in shrimp larvae and parental spawners. In view of these points the present researches are focused on the WSBV genomic structure and on the development of rapid and sensitive diagnostic tools.

In experiment, shrimp DNA specific primers are used in several assessments. The aims of the use of shrimp DNA specific primer set in the present study were (i) to assess the purity of WSBV genomic DNA preparations, (ii) to evaluate nucleic acid extraction procedures for yielding amplificable DNA template, and (iii) to estimate approximately the proportion of the shrimp DNA and WSBV DNA in template DNAs prepared from total nucleic acids of the infected tissues. Attempts have been made in our laboratory to purify WSBV virions from various tissues including epidermis, muscle and gills. From these virions we obtained WSBV DNA of varied purity as assessed by shrimp DNA specific primers. Examples of these assessments are shown in FIGS. 13 and 17. The nucleic acids extracted from muscle tissues yielded a great quantity of WSBV DNA, but were heavily contaminated with shrimp DNA (FIG. 16, lane 9). The virions purified from heavily infected epidermal cells underneath the exoskeleton are good starting materials for extracting "super pure" WSBV genomic DNA (FIG. 16 lanes 2 and 5). By using the shrimp DNA specific primers and PCR, for the first time a tool is available to assess the extent of the shrimp DNA contamination in shrimp virus genomic DNA preparations.

Figure 20:
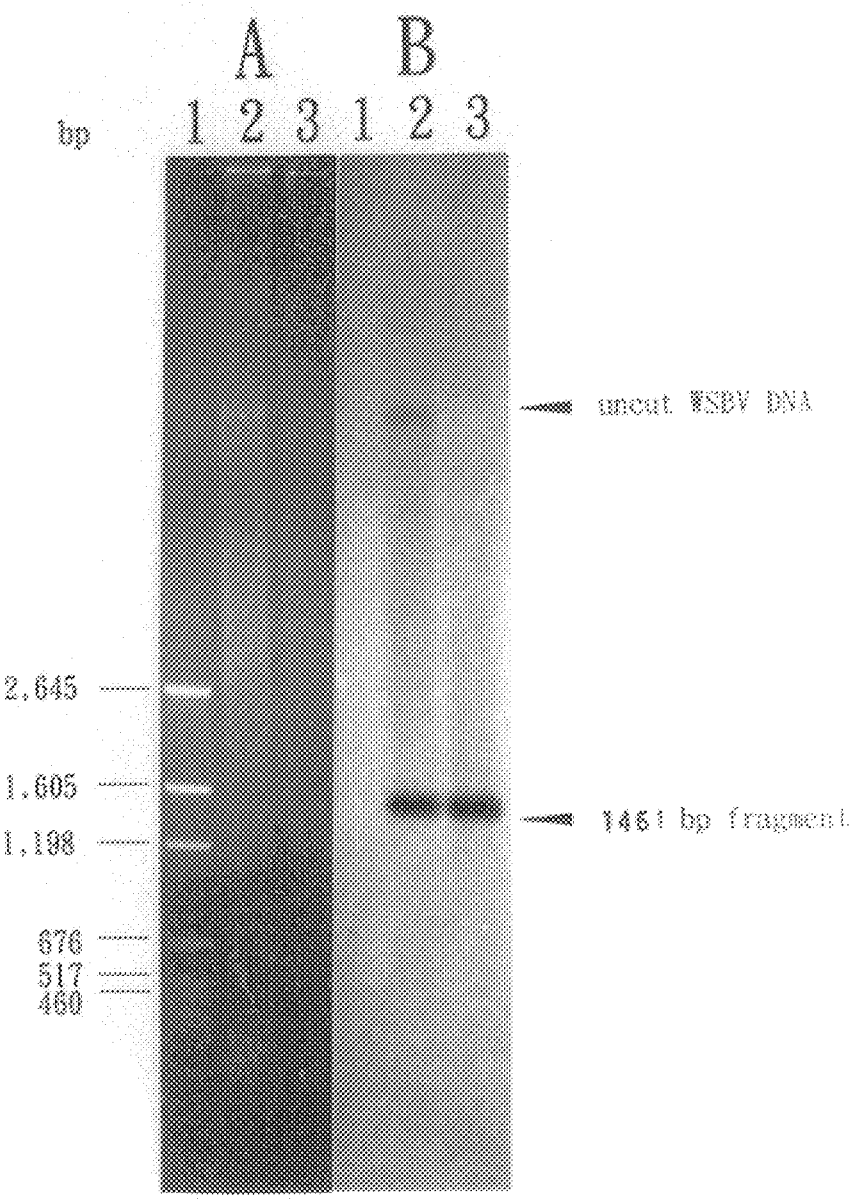

Using the WSBV DNA specific primers, all the purified WSBV genomic DNA samples consistently yielded an evident amplification product showing the expected mobility of a 1447-kbp DNA fragment. The nucleic acids extracted from tissues of naturally diseased shrimp with white spot syndrome and from shrimp experimentally infected with WSBV also consistently gave PCR products of the same size. The nucleic acids extracted from the tissues of clinically healthy shrimp showed no positive results. These results demonstrate the specificity of the WSBV DNA specific primers designed in the present study. In addition, the 1447-bp PCR product can be used to prepared WSBV specific nucleic acid probe for detecting WSBV infection in shrimp using dot blot hybridization as shown in FIG. 19. Piratically, the present studies provide three effective diagnostic tools for screening of the WSBV infection in penaeid shrimps as shown in FIGS. 17, 19 and 20.

With PCR (FIG. 17) and Southern hybridization (FIG. 20), we have demonstrated that the causative agents of white spot syndrome of different shrimp species are in fact closely related. Screening for the WSBV infection in shrimp should be undertaken immediately in order to prevent this viral disease from spreading further. On the other hand, the PCR diagnostic techniques for WSBV developed in the present study provide effective tools for the comparative studies on the shrimp non-occluded baculoviruses such as Japan' RV-PJ (Inouye et al (1994), supra), China' HHNBV ( Cai et al., J. Fish. China, 19: 112–117, 1995), Thailand' SEMBV (Wongteerasupaya et al. (1995), supra), the present WSBV isolate PmNOBIII and other crustacean nonnonnon-occluded baculoviruses.

From the above teachings, it is apparent that various modifications and variations can be made without departing from the spirit and scope of the present invention. It is therefore to be understood that this invention may be practiced otherwise than as specifically described.

TABLE 1

The insert size (in kilo base pair; kb) of clones in PmNOBIII SalI (pms) and PmNOBIII HindIII (pmh) libraries.

| clone no. | PmNOB SalI library (pms) insert size (kb) | clone no. | PmNOB HindIII library (pmh) insert size (kb) |
|---|---|---|---|
| pms1 | 0–0.1 | pmh1 | 0.3 |
| pms2 | 0–0.1 | pmh2 | 7–8 |
| pms3 | 0–0.1 | pmh3 | 4 |
| pms4 | 0–0.1 | pmh4 | 0–0.1 |
| pms5 | 0–0.1 | pmh5 | 0–0.1 |
| pms6 | 0–0.1 | pmh6 | 0–0.1 |
| pms7 | 4 | pmh7 | 5 |
| pms8 | ? | pmh8 | 3 |
| pms9 | 0–0.1 | pmh9 | ? |
| pms10 | 0–0.1 | pmh10 | 9 |
| pms11 | 0–0.1 | pmh11 | 7–8 |
| pms12 | 0–0.1 | pmh12 | 3.5 |
| pms13 | 0–0.1 | pmh13 | 9–23 |
| pms14 | 0–0.1 | pmh14 | 2.2 |
| pms15 | 0–0.1 | pmh15 | 4 |
| pms16 | 0–0.1 | pmh16 | 6 |
| pms17 | 3 | pmh17 | 7 |
| pms18 | 0–0.1 | pmh18 | 6 |

TABLE 1-continued

The insert size (in kilo base pair; kb) of clones in PmNOBIII SalI (pms) and PmNOBIII HindIII (pmh) libraries.

| clone no. | PmNOB SalI library (pms) insert size (kb) | clone no. | PmNOB HindIII library (pmh) insert size (kb) |
|---|---|---|---|
| pms19 | ? | pmh19 | 7 |
| pms20 | ? | pmh20 | 1.5 |
| pms21 | 0–0.1 | pmh21 | 1.7 |
| pms22 | ? | pmh22 | 8 |
| pms23 | 0–0.1 | pmh23 | 2.2 |
| pms24 | ? | pmh24 | 0–0.1 |
| pms25 | ? | pmh25 | 0–0.1 |
| pms26 | 0–0.1 | pmh26 | 0–0.1 |
| pms27 | 0–0.1 | pmh27 | 2.2 |
| pms28 | 0–0.1 | pmh28 | 6 |
| pms29 | 0–0.1 | pmh29 | 0–0.1 |
| pms30 | 0–0.1 | pmh30 | 5 |
| pms31 | 0–0.1 | pmh31 | 4 |
| pms32 | 0–0.1 | pmh32 | 9 |
| pms33 | 0–0.1 | pmh33 | 6 |
| pms34 | 0–0.1 | pmh34 | 7–8 |
| pms35 | 0–0.1 | pmh35 | 0.5 |
| pms36 | 0–0.1 | pmh36 | ? |
| pms37 | 0–0.1 | pmh37 | 3.5 |
| pms38 | 0–0.1 | pmh38 | 1.5 |
| pms39 | 0–0.1 | pmh39 | 4 |
| pms40 | 4 | pmh40 | 6 |
| pms41 | 0–0.1 | pmh41 | 6 |
| pms42 | 0–0.1 | pmh42 | 1.5 |
| pms43 | 0–0.1 | pmh43 | 1 |
| pms44 | ? | pmh44 | 0–0.1 |
| pms45 | 0–0.1 | pmh45 | 6 |
| pms46 | 0–0.1 | pmh46 | ? |
| pms47 | 0–0.1 | pmh47 | 1.7 |
| pms48 | 0–0.1 | pmh48 | 3 |
| pms49 | 3 | pmh49 | 8 |
| pms50 | ? | pmh50 | 2.2 |
| pms51 | ? | pmh51 | 0–0.1 |
| pms52 | 2 | pmh52 | 4 |
| pms53 | 0–0.1 | pmh53 | 0–0.1 |
| pms54 | 5–6 | pmh54 | 0–0.1 |
| pms55 | 0–0.1 | pmh55 | 8 |
| pms56 | 2 | pmh56 | 3.5 |
| pms57 | 0.5 | pmh57 | ? |
| pms58 | 0–0.1 | pmh58 | 5 |
| pms59 | ? | pmh59 | 3.5 |
| pms60 | 4–5 | pmh60 | 0–0.1 |
| pms61 | ? | pmh61 | 3.2 |
| pms62 | 0–0.1 | pmh62 | 2 |
| pms63 | 0.5–1 | pmh63 | 0–0.1 |
| pms64 | 0–0.1 | pmh64 | 4 |
| pms65 | 2–3 | pmh65 | 6 |
| pms66 | 1.5 | pmh66 | 3.5 |
| pms67 | 0–0.1 | pmh67 | 1.5 |
| pms68 | 0.5 | pmh68 | ? |
| pms69 | 0.3 | pmh69 | 4.4 |
| pms70 | 0.2 | pmh70 | 7 |
| pms71 | ? | pmh71 | ? |
| pms72 | 0.5 | pmh72 | ? |
| pms73 | ? | pmh73 | 7 |
| pms74 | 0–0.1 | pmh74 | ? |
| pms75 | 0–0.1 | pmh75 | ? |
| pms76 | 5–6 | pmh76 | ? |
| pms77 | 0–0.1 | pmh77 | ? |
| pms78 | 0.2 | pmh78 | 0–0.1 |
| pms79 | ? | pmh79 | ? |
| pms80 | 0.3 | pmh80 | ? |
| pms81 | ? | pmh81 | ? |
| pms82 | 0.5 | pmh82 | ? |
| pms83 | 3 | pmh83 | ? |
| pms84 | ? | pmh84 | 4.4 |
| pms85 | ? | pmh85 | ? |
| pms86 | 3 | pmh86 | ? |
| pms87 | ? | pmh87 | ? |
| pms88 | ? | pmh88 | ? |
| pms89 | ? | pmh89 | 0–0.1 |
| pms90 | ? | pmh90 | ? |
| pms91 | 0.3 | pmh91 | ? |
| pms92 | 6 | pmh92 | ? |
| pms93 | 0.2 | pmh93 | 9 |
| pms94 | 9 | pmh94 | 8 |
| pms95 | 0–0.1 | pmh95 | ? |
| pms96 | ? | pmh96 | ? |
| pms97 | 0.3 | pmh97 | ? |
| pms98 | 4 | pmh98 | 1.5 |
| pms99 | 0–0.1 | pmh99 | ? |
| pms100 | 6 | pmh100 | ? |
| pms101 | ? | pmh101 | 0–0.1 |
| pms102 | 0.3 | pmh102 | 7 |
| pms103 | 7–8 | pmh103 | 1.5 |
| pms104 | ? | pmh104 | 1 |
| pms105 | ? | pmh105 | 9 |
| pms106 | 2 | pmh106 | ? |
| pms107 | 0–0.1 | pmh107 | 2.2 |
| pms108 | 0–0.1 | pmh108 | 0.5 |
| pms109 | 3–4 | pmh109 | 0–0.1 |
| pms110 | 3 | pmh110 | 0–0.1 |
| pms111 | 3–4 | pmh111 | ? |
| pms112 | 1.5 | pmh112 | ? |
| pms113 | 2 | pmh113 | ? |
| pms114 | ? | pmh114 | ? |
| pms115 | 8 | pmh115 | 2.2 |
| pms116 | 2 | pmh116 | ? |
| pms117 | ? | pmh117 | ? |
| pms118 | ? | pmh118 | ? |
| pms119 | 0–0.1 | pmh119 | 9–23 |
| pms120 | 4 | pmh120 | 2.5 |
| pms121 | 0–0.1 | pmh121 | ? |
| pms122 | 3 | pmh122 | ? |
| pms123 | 0–0.1 | pmh123 | ? |
| pms124 | 4 | pmh124 | ? |
| pms125 | 0–0.1 | pmh125 | ? |
| pms126 | ? | pmh126 | ? |
| pms127 | ? | pmh127 | ? |
| pms128 | 0–0.1 | pmh128 | ? |
| pms129 | ? | pmh129 | ? |
| pms130 | 3 | pmh130 | ? |
| pms131 | 0–0.1 | pmh131 | ? |
| pms132 | ? | pmh132 | ? |
| pms133 | ? | pmh133 | ? |
| pms134 | 7–8 | pmh134 | ? |
| pms135 | 0–0.1 | pmh135 | ? |
| pms136 | ? | pmh136 | ? |
| pms137 | ? | pmh137 | 6 |
| pms138 | ? | pmh138 | 2 |
| pms139 | ? | pmh139 | ? |
| pms140 | ? | pmh140 | 0–0.1 |
| pms141 | 2 | pmh141 | ? |
| pms142 | ? | pmh142 | 4 |
| pms143 | ? | pmh143 | 0–0.1 |
| pms144 | ? | pmh144 | ? |
| pms145 | ? | pmh145 | 0–0.1 |
| pms146 | 1.5 | pmh146 | ? |
| pms147 | ? | pmh147 | ? |
| pms148 | ? | pmh148 | ? |
| pms149 | ? | pmh149 | 0–0.1 |
| pms150 | ? | pmh150 | ? |
| pms151 | 0.2 | pmh151 | 7 |
| pms152 | ? | pmh152 | 2.2 |
| pms153 | ? | pmh153 | ? |
| pms154 | ? | pmh154 | ? |
| pms155 | ? | pmh155 | ? |
| pms156 | ? | pmh156 | ? |
| pms157 | ? | pmh157 | ? |
| pms158 | ? | pmh158 | ? |
| pms159 | 0.2 | pmh159 | 0–0.1 |
| pms160 | 1 | pmh160 | ? |
| pms161 | ? | pmh161 | ? |
| pms162 | 0.3 | pmh162 | 0–0.1 |

TABLE 1-continued

The insert size (in kilo base pair; kb) of clones in PmNOBIII SalI (pms) and PmNOBIII HindIII (pmh) libraries.

| clone no. | PmNOB SalI library (pms) insert size (kb) | clone no. | PmNOB HindIII library (pmh) insert size (kb) |
|---|---|---|---|
| pms163 | 0–0.1 | pmh163 | 0–0.1 |
| pms164 | 4 | pmh164 | 5 |
| pms165 | 0–0.1 | pmh165 | ? |
| pms166 | 0–0.1 | pmh166 | ? |
| pms167 | 0.2 | pmh167 | 1 |
| pms168 | 1.5 | pmh168 | 7 |
| pms169 | 0–0.1 | pmh169 | ? |
| pms170 | 0.5 | pmh170 | 1 |
| pms171 | 0–0.1 | pmh171 | ? |
| pms172 | 0–0.1 | pmh172 | ? |
| pms173 | 0.3 | pmh173 | ? |
| pms174 | 0–0.1 | pmh174 | ? |
| pms175 | 0–0.1 | pmh175 | 1.3 |
| pms176 | 0–0.1 | pmh176 | ? |
| pms177 | 0–0.1 | pmh177 | ? |
| pms178 | 0–0.1 | pmh178 | 6 |
| pms179 | 0–0.1 | pmh179 | 3 |
| pms180 | 1.5 | pmh180 | 3 |
| pms181 | 4 | pmh181 | ? |
| pms182 | 0.5 | pmh182 | 9 |
| pms183 | 0.5 | pmh183 | 0–0.1 |
| pms184 | 0–0.1 | pmh184 | ? |
| pms185 | 0.5 | pmh185 | 4.4 |
| pms186 | 0–0.1 | pmh186 | 0–0.1 |
| pms187 | 0–0.1 | pmh187 | 9 |
| pms188 | 0–0.1 | pmh188 | 1 |
| pms189 | 2 | pmh189 | ? |
| pms190 | 0–0.1 | pmh190 | ? |
| pms191 | 0–0.1 | pmh191 | ? |
| pms192 | 0–0.1 | pmh192 | ? |
| pms193 | 0–0.1 | pmh193 | ? |
| pms194 | 0–0.1 | pmh194 | ? |
| pms195 | >9 | pmh195 | ? |
| pms196 | 0–0.1 | pmh196 | 1.5 |
| pms197 | 1.5 | pmh197 | ? |
| pms198 | 0–0.1 | pmh198 | ? |
| pms199 | ? | pmh199 | ? |
| pms200 | ? | pmh200 | 1.7 |
| pms201 | 0–0.1 | pmh201 | 1 |
| pms202 | ? | pmh202 | 9 |
| pms203 | 1.5 | pmh203 | 6 |
| pms204 | ? | pmh204 | 4.5 |
| pms205 | ? | pmh205 | 7 |
| pms206 | ? | pmh206 | 7 |
| pms207 | 0.3 | pmh207 | 7 |
| pms208 | ? | pmh208 | 8 |
| pms209 | 0.3 | pmh209 | 7 |
| pms210 | 0.3 | pmh210 | 4.5 |
| pms211 | ? | pmh211 | 3.2 |
| pms212 | ? | pmm212 | 3.2 |
| pms213 | 0–0.1 | pmh213 | 4.4 |
| pms214 | 1.5 | pmh214 | 1.5 |
| pms215 | ? | pmh215 | 3 |
| pms216 | 4 | pmh216 | 4.5 |
| pms217 | ? | pmh217 | 3 |
| pms218 | 1 | pmh218 | 7 |
| pms219 | 0–0.1 | pmh219 | 3 |
| pms220 | ? | pmh220 | 3.2 |
| pms221 | ? | pmh221 | 2.2 |
| pms222 | ? | pmh222 | 2.2 |
| pms223 | ? | pmh223 | 2.4 |
| pms224 | ? | pmh224 | 1.7 |
| pms225 | 0.5 | pmh225 | 4.2 |
| pms226 | ? | pmh226 | 2.2 |
| pms227 | 0.3 | pmh227 | 4.2 |
| pms228 | 0.3 | pmh228 | 4 |
| pms229 | ? | pmh229 | 1.5 |
| pms230 | 0–0.1 | pmh230 | 2.2 |
| pms231 | 7–8 | pmh231 | 2.2 |
| pms232 | 0.3 | pmh232 | 4.2 |
| pms233 | 0.3 | pmh233 | 2.2 |
| pms234 | 0–0.1 | pmh234 | 1.5 |
| pms235 | 0.5 | pmh235 | 4.2 |
| pms236 | 0.4 | pmh236 | 2.2 |
| pms237 | 0.3 | pmh237 | 2.2 |
| pms238 | 1.5 | pmh238 | 4.4 |
| pms239 | 3 | pmh239 | 3 |
| pms240 | 1 | pmh240 | 3 |
| pms241 | 0.5 | pmh241 | 2.6 |
| pms242 | 0.3 | pmh242 | 5 |
| pms243 | ? | pmh243 | 3 |
| pms244 | 0–0.1 | pmh244 | 2.5 |
| pms245 | 0.5 | pmh245 | 3.2 |
| pms246 | 0–0.1 | pmh246 | |
| pms247 | ? | pmh247 | |
| pms248 | 0.5 | pmh248 | |
| pms249 | 7–8 | pmh249 | |
| pms250 | 4–5 | pmh250 | |
| pms251 | 0.3 | pmh251 | |
| pms252 | 0–0.1 | pmh252 | |
| pms253 | 0.2 | pmh253 | |
| pms254 | 0–0.1 | pmh254 | |
| pms255 | 0.3 | pmh255 | |
| pms256 | 0.2 | pmh256 | |
| pms257 | ? | pmh257 | |
| pms258 | 0.5 | pmh258 | |
| pms259 | 0.4 | pmh259 | |
| pms260 | 0–0.1 | pmh260 | |
| pms261 | ? | pmh261 | |
| pms262 | 0.3 | pmh262 | |
| pms263 | ? | pmh263 | |
| pms264 | 2.5 | pmh264 | |
| pms265 | ? | pmh265 | |
| pms266 | 0–0.1 | pmh266 | |
| pms267 | 7–8 | pmh267 | |
| pms268 | 0.2 | pmh268 | |
| pms269 | ? | pmh269 | |
| pms270 | ? | pmh270 | |
| pms271 | 0–0.1 | pmh271 | |
| pms272 | ? | pmh272 | |
| pms273 | 0–0.1 | pmh273 | |
| pms274 | 3 | pmh274 | |
| pms275 | ? | pmh275 | |
| pms276 | ? | pmh276 | |
| pms277 | 4–5 | pmh277 | |
| pms278 | 0–0.1 | pmh278 | |
| pms279 | 0–0.1 | pmh279 | |
| pms280 | 0–0.1 | pmh280 | |
| pms281 | ? | pmh281 | |
| pms282 | ? | pmh282 | |
| pms283 | 0–0.1 | pmh283 | |
| pms284 | ? | pmh284 | |
| pms285 | 0–0.1 | pmh285 | |
| pms286 | 0.2 | pmh286 | |
| pms287 | 0.2 | pmh287 | |
| pms288 | ? | pmh288 | |
| pms289 | 4 | pmh289 | |
| pms290 | 0–0.1 | pmh290 | |
| pms291 | 3.5 | pmh291 | |
| pms292 | 1.5 | pmh292 | |
| pms293 | 3 | pmh293 | |
| pms294 | 0–0.1 | pmh294 | |
| pms295 | 1.5 | pmh295 | |
| pms296 | 6 | pmh296 | |
| pms297 | 4–5 | pmh297 | |
| pms298 | ? | pmh298 | |
| pms299 | ? | pmh299 | |
| pms300 | 0–0.1 | pmh300 | |
| pms301 | 0.2 | pmh301 | |
| pms302 | 0.3 | pmh302 | |
| pms303 | 0.3 | pmh303 | |
| pms304 | 0–0.1 | pmh304 | |
| pms305 | 0–0.1 | pmh305 | |
| pms306 | 0.3 | pmh306 | |

TABLE 1-continued

The insert size (in kilo base pair; kb) of clones in PmNOBIII SalI (pms) and PmNOBIII HindIII (pmh) libraries.

| clone no. | PmNOB SalI library (pms) insert size (kb) | clone no. | PmNOB HindIII library (pmh) insert size (kb) |
|---|---|---|---|
| pms307 | ? | pmh307 | |
| pms308 | ? | pmh308 | |
| pms309 | 0.5 | pmh309 | |
| pms310 | 0–0.1 | pmh310 | |
| pms311 | 0.5 | pmh311 | |
| pms312 | 6 | pmh312 | |
| pms313 | 3 | pmh313 | |
| pms314 | ? | pmh314 | |
| pms315 | ? | pmh315 | |
| pms316 | 0–0.1 | pmh316 | |
| pms317 | ? | pmh317 | |
| pms318 | ? | pmh318 | |
| pms319 | 0–0.1 | pmh319 | |
| pms320 | ? | pmh320 | |
| pms321 | 4–5 | pmh321 | |
| pms322 | 0.5 | pmh322 | |
| pms323 | ? | pmh323 | |
| pms324 | 4 | pmh324 | |
| pms325 | 0.2 | pmh325 | |
| pms326 | 2 | pmh326 | |
| pms327 | 1 | pmh327 | |
| pms328 | 0–0.1 | pmh328 | |
| pms329 | ? | pmh329 | |
| pms330 | ? | pmh330 | |
| pms331 | 4–5 | pmh331 | |
| pms332 | 0.2 | pmh332 | |
| pms333 | ? | pmh333 | |
| pms334 | 2 | pmh334 | |
| pms335 | 0–0.1 | pmh335 | |
| pms336 | 0.2 | pmh336 | |
| pms337 | 0–0.1 | pmh337 | |
| pms338 | ? | pmh338 | |
| pms339 | 0–0.1 | pmh339 | |
| pms340 | ? | pmh340 | |
| pms341 | 0–0.1 | pmh341 | |
| pms342 | ? | pmh342 | |
| pms343 | 0–0.1 | pmh343 | |
| pms344 | ? | pmh344 | |
| pms345 | 2 | pmh345 | |
| pms346 | 0–0.1 | pmh346 | |
| pms347 | 0–0.1 | pmh347 | |
| pms348 | 0.2 | pmh348 | |
| pms349 | 0.5 | pmh349 | |
| pms350 | 0–0.1 | pmh350 | |
| pms351 | 4 | pmh351 | |
| pms352 | 0–0.1 | pmh352 | |
| pms353 | 0.3 | pmh353 | |
| pms354 | 0–0.1 | pmh354 | |
| pms355 | 0–0.1 | pmh355 | |
| pms356 | 0–0.1 | pmh356 | |
| pms357 | 0–0.1 | pmh357 | |
| pms358 | 0–0.1 | pmh358 | |
| pms359 | 0–0.1 | pmh359 | |
| pms360 | ? | pmh360 | |
| pms361 | 0–0.1 | pmh361 | |
| pms362 | ? | pmh362 | |
| pms363 | ? | pmh363 | |
| pms364 | ? | pmh364 | |
| pms365 | ? | pmh365 | |
| pms366 | 0–0.1 | pmh366 | |
| pms367 | ? | pmh367 | |
| pms368 | ? | pmh368 | |
| pms369 | 0–0.1 | pmh369 | |
| pms370 | ? | pmh370 | |
| pms371 | 0.5 | pmh371 | |
| pms372 | 0.3 | pmh372 | |
| pms373 | 0.5 | pmh373 | |
| pms374 | ? | pmh374 | |
| pms375 | ? | pmh375 | |
| pms376 | 3 | pmh376 | |
| pms377 | ? | pmh377 | |
| pms378 | 6 | pmh378 | |
| pms379 | ? | pmh379 | |
| pms380 | ? | pmh380 | |
| pms381 | 4 | pmh381 | |
| pms382 | ? | pmh382 | |
| pms383 | ? | pmh383 | |
| pms384 | ? | pmh384 | |
| pms385 | 0–0.1 | pmh385 | |
| pms386 | ? | pmh386 | |
| pms387 | ? | pmh387 | |
| pms388 | ? | pmh388 | |
| pms389 | ? | pmh389 | |
| pms390 | ? | pmh390 | |
| pms391 | 0–0.1 | pmh391 | |
| pms392 | ? | pmh392 | |
| pms393 | ? | pmh393 | |
| pms394 | ? | pmh394 | |
| pms395 | 0–0.1 | pmh395 | |
| pms396 | 0–0.1 | pmh396 | |
| pms397 | 0–0.1 | pmh397 | |
| pms398 | ? | pmh398 | |
| pms399 | ? | pmh399 | |
| pms400 | 0–0.1 | pmh400 | |
| pms401 | ? | pmh401 | |
| pms402 | 0.2 | pmh402 | |
| pms403 | 0–0.1 | pmh403 | |
| pms404 | 0–0.1 | pmh404 | |
| pms405 | 0–0.1 | pmh405 | |
| pms406 | 0–0.1 | pmh406 | |
| pms407 | ? | pmh407 | |
| pms408 | 0.5 | pmh408 | |
| pms409 | ? | pmh409 | |
| pms410 | 0.5 | pmh410 | |
| pms411 | 0–0.1 | pmh411 | |
| pms412 | 1 | pmh412 | |
| pms413 | 0.2 | pmh413 | |
| pms414 | 4.5 | pmh414 | |
| pms415 | 6 | pmh415 | |
| pms416 | 0–0.1 | pmh416 | |
| pms417 | 0–0.1 | pmh417 | |
| pms418 | 4 | pmh418 | |
| pms419 | 0–0.1 | pmh419 | ? |
| pms420 | 2 | pmh420 | 1.7 |
| pms421 | 0.2 | pmh421 | 6 |
| pms422 | 0.5 | pmh422 | 9 |
| pms423 | 0–0.1 | pmh423 | ? |
| pms424 | 0–0.1 | pmh424 | 0–0.1 |
| pms425 | 1.2 | pmh425 | 0–0.1 |
| pms426 | ? | pmh426 | 0–0.1 |
| pms427 | 4.5 | pmh427 | 4 |
| pms428 | 0–0.1 | pmh428 | 7 |
| pms429 | 6 | pmh429 | ? |
| pms430 | 0.3 | pmh430 | 3.5 |
| pms431 | 0.5 | pmh431 | 8 |
| pms432 | 0–0.1 | pmh432 | 1.5 |
| pms433 | 0.2 | pmh433 | 4 |
| pms434 | 0–0.1 | pmh434 | ? |
| pms435 | 0–0.1 | pmh435 | 7 |
| pms436 | 0.2 | pmh436 | 4.4 |
| pms437 | 0–0.1 | pmh437 | 0–0.1 |
| pms438 | 0–0.1 | pmh438 | 6 |
| pms439 | 0.5 | pmh439 | 5 |
| pms440 | 0–0.1 | pmh440 | ? |
| pms441 | 2 | pmh441 | 7 |
| pms442 | ? | pmh442 | ? |
| pms443 | 2.5 | pmh443 | ? |
| pms444 | 4.5 | pmh444 | 0–0.1 |
| pms445 | 0.2 | pmh445 | 2 |
| pms446 | 4.5 | pmh446 | ? |
| pms447 | 3 | pmh447 | 9–23 |
| pms448 | 0–0.1 | pmh448 | 1.5 |
| pms449 | 0–0.1 | pmh449 | 3.2 |
| pms450 | 0–0.1 | pmh450 | 0–0.1 |

TABLE 1-continued

The insert size (in kilo base pair; kb) of clones in PmNOBIII SalI (pms) and PmNOBIII HindIII (pmh) libraries.

| clone no. | PmNOB SalI library (pms) insert size (kb) | clone no. | PmNOB HindIII library (pmh) insert size (kb) |
|---|---|---|---|
| pms451 | 0–0.1 | pmh451 | 0–0.1 |
| pms452 | 0.5 | pmh452 | ? |
| pms453 | 0–0.1 | pmh453 | 4.4 |
| pms454 | 0.3 | pmh454 | 1 |
| pms455 | 0–0.1 | pmh455 | 1 |
| pms456 | 0–0.1 | pmh456 | 0–0.1 |
| pms457 | 0–0.1 | pmh457 | ? |
| pms458 | 3 | pmh458 | ? |
| pms459 | 0.5 | pmh459 | ? |
| pms460 | 4–5 | pmh460 | ? |
| pms461 | 0–0.1 | pmh461 | ? |
| pms462 | 3–4 | pmh462 | ? |
| pms463 | 0–0.1 | pmh463 | ? |
| pms464 | 0–0.1 | pmh464 | ? |
| pms465 | 0–0.1 | pmh465 | ? |
| pms466 | 5 | pmh466 | 2.6 |
| pms467 | 0–0.1 | pmh467 | ? |
| pms468 | 6 | pmh468 | 4.2 |
| pms469 | 0–0.1 | pmh469 | 2.4 |
| pms470 | 5 | pmh470 | 4 |
| pms471 | 9 | pmh471 | 4.4 |
| pms472 | 0–0.1 | pmh472 | 8 |
| pms473 | 9–23 | pmh473 | 3 |
| pms474 | 0–0.1 | pmh474 | 4 |
| pms475 | 0.5 | pmh475 | 4.7 |
| pms476 | 0–0.1 | pmh476 | ? |
| pms477 | 5 | pmh477 | ? |
| pms478 | 0–0.1 | pmh478 | ? |
| pms479 | 0–0.1 | pmh479 | ! |
| pms480 | 0.3 | pmh480 | 2 |
| pms481 | 1 | pmh481 | ? |
| pms482 | 5 | pmh482 | 0–0.1 |
| pms483 | 1.5 | pmh483 | ? |
| pms484 | 9 | pmh484 | 2.2 |
| pms485 | 0.2 | pmh485 | 1.5 |
| pms486 | 0–0.1 | pmh486 | 2.2 |
| pms487 | 0–0.1 | pmh487 | ? |
| pms488 | 1.5 | pmh488 | 2.2 |
| pms489 | 5 | pmh489 | ? |
| pms490 | 0–0.1 | pmh490 | 4 |
| pms491 | 1.5 | pmh491 | 1.5 |
| pms492 | 0–0.1 | pmh492 | 4.8 |
| pms493 | 0–0.1 | pmh493 | ? |
| pms494 | 9 | pmh494 | ? |
| pms495 | 0.2 | pmh495 | ? |
| pms496 | 0–0.1 | pmh496 | 0–0.1 |
| pms497 | 1.5 | pmh497 | 0.5 |
| pms498 | 0–0.1 | pmh498 | ? |
| pms499 | 0.3 | pmh499 | 7 |
| pms500 | 0.5 | pmh500 | 0–0.1 |
| pms501 | 0–0.1 | pmh501 | ? |
| pms502 | 0–0.1 | pmh502 | 2.6 |
| pms503 | 0–0.1 | pmh503 | 1.8 |
| pms504 | 0–0.1 | pmh504 | 0.5 |
| pms505 | 0–0.1 | pmh505 | 2.2 |
| pms506 | 3 | pmh506 | ? |
| pms507 | 0.3 | pmh507 | 1.8 |
| pms508 | 0.2 | pmh508 | ? |
| pms509 | 3 | pmh509 | 0.7 |
| pms510 | 5 | pmh510 | 2.3 |
| pms511 | 0–0.1 | pmh511 | ? |
| pms512 | 0.5 | pmh512 | 9–23 |
| pms513 | 0–0.1 | pmh513 | 1.5 |
| pms514 | 4 | pmh514 | ? |
| pms515 | 0–0.1 | pmh515 | 3.2 |
| pms516 | 6 | pmh516 | 8 |
| pms517 | 0–0.1 | pmh517 | ? |
| pms518 | 0–0.1 | pmh518 | 0–0.1 |
| pms519 | 0.2 | pmh519 | 3.5 |
| pms520 | 0–0.1 | pmh520 | 4.4 |
| pms521 | 0.3 | pmh521 | ? |
| pms522 | 5 | pmh522 | 5 |
| pms523 | 0.6 | pmh523 | 4.4 |
| pms524 | 0.3 | pmh524 | 7 |
| pms525 | 0–0.1 | pmh525 | 1.5 |
| pms526 | 6 | pmh526 | 5.5 |
| pms527 | 0–0.1 | pmh527 | 1.5 |
| pms528 | 6 | pmh528 | 7 |
| pms529 | 0.2 | pmh529 | 4.4 |
| pms530 | 3 | pmh530 | 7 |
| pms531 | 3 | pmh531 | 2.2 |
| pms532 | 0–0.1 | pmh532 | 8 |
| pms533 | 0–0.1 | pmh533 | 9 |
| pms534 | 5 | pmh534 | 1.5 |
| pms535 | 0–0.1 | pmh535 | ? |
| pms536 | 5 | pmh536 | 1.5 |
| pms537 | 0–0.1 | pmh537 | ? |
| pms538 | 2 | pmh538 | ? |
| pms539 | 0–0.1 | pmh539 | 2.2 |
| pms540 | 0–0.1 | pmh540 | ? |
| pms541 | 0–0.1 | pmh541 | ? |
| pms542 | 0–0.1 | pmh542 | 4.6 |
| pms543 | 3 | pmh543 | 0–0.1 |
| pms544 | 4 | pmh544 | 1.5 |
| pms545 | 0–0.1 | pmh545 | 8 |
| pms546 | 0–0.1 | pmh546 | 9 |
| pms547 | 0–0.1 | pmh547 | 1.5 |
| pms548 | 1.5 | pmh548 | 0.2 |
| pms549 | 3 | pmh549 | 0.5 |
| pms550 | 4.4 | pmh550 | ? |
| pms551 | 0–0.1 | pmh551 | 0–0.1 |
| pms552 | 0–0.1 | pmh552 | 5.5 |
| pms553 | 0–0.1 | pmh553 | 3 |
| pms554 | 0–0.1 | pmh554 | 0–0.1 |
| pms555 | 4.4 | pmh555 | 7 |
| pms556 | 0–0.1 | pmh556 | ? |
| pms557 | 0–0.1 | pmh557 | ? |
| pms558 | 3 | pmh558 | 2.6 |
| pms559 | 0–0.1 | pmh559 | ? |
| pms560 | 0.5 | pmh560 | ? |
| pms561 | 0–0.1 | pmh561 | 0–0.1 |
| pms562 | 2 | pmh562 | 4 |
| pms563 | 0–0.1 | pmh563 | 2.2 |
| pms564 | 0–0.1 | pmh564 | ? |
| pms565 | 0–0.1 | pmh565 | ? |
| pms566 | 6 | pmh566 | ? |
| pms567 | 9 | pmh567 | ? |
| pms568 | 0.3 | pmh568 | ? |
| pms569 | 0.5 | pmh569 | ? |
| pms570 | 0.2 | pmh570 | 5 |
| pms571 | 0.5 | pmh571 | 4 |
| pms572 | 0–0.1 | pmh572 | ? |
| pms573 | 0–0.1 | pmh573 | ? |
| pms574 | 0.2 | pmh574 | 7 |
| pms575 | 0.3 | pmh575 | 5.5 |
| pms576 | 3 | pmh576 | 8 |
| pms577 | 0.5 | pmh577 | 9 |
| pms578 | 0–0.1 | pmh578 | 0–0.1 |
| pms579 | 0–0.1 | pmh579 | 9 |
| pms580 | 0–0.1 | pmh580 | 0–0.1 |
| pms581 | ? | pmh581 | ? |
| pms582 | ? | pmh582 | 0–0.1 |
| pms583 | ? | pmh583 | 5 |
| pms584 | ? | pmh584 | 4 |
| pms585 | ? | | |
| pms586 | ? | | |
| pms587 | ? | | |
| pms588 | ? | | |
| pms589 | ? | | |
| pms590 | 0–0.1 | | |
| pms591 | 0–0.1 | | |
| pms592 | ? | | |

We claim:

1. A method for obtaining a viral isolate of non-occluded baculovirus (NOB) from a host organism infected thereby, comprising the steps of:
   a) obtaining a sample from a host organism infected with a NOB virus;
   b) treating the sample with protease inhibitors in an amount to inhibit the degradation of the NOB virus; and
   c) purifying the virus.

2. A method according to claim 1, wherein the purification step (c) is performed by centrifugation.

3. A method according to claim 2, wherein the purification step (c) is performed by sucrose gradient centrifugation.

4. A method according to claim 2, wherein the protease inhibitors are removed post centrifugation.

5. A method according to claim 1, wherein the viral isolate of NOB is of the WSBV species.

6. A method according to claim 5, wherein the viral isolate is PmNOBIII.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1461 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
GTCGACAGAC  TACTAACTTC  AGCCTATCTA  GTAAAACAAG  CTAAAAGATT  CGACGGAGTT      60
GACCCAGCCT  TCCCTGCCGC  CCTCACCTGC  GCTTCTCACC  TCATGCTTTC  TTCCATGGAT     120
TCCCATACAA  AGTCATCTTT  CATGGACAAC  ATCAAATTGC  ACATGACTGA  TACTCAATGC     180
TTCTTCAAGA  ACATTGAACG  ATTTGAGAAA  TTCTTGGGAA  GATATGGGGA  CGAATACGCC     240
ATGTCCCACA  AGCAAAATTG  TAACTGCCCC  TTCCATCTCC  ACCACACTTT  TACTCCCTCA     300
GATAACGAGC  ATCTGGTATC  CTCTTTCGCA  TTCGCCCGCC  CAGAAGTCTC  CATGGAAGAA     360
ATTAGAGCCA  CACCCTATCA  GGCCAACAAG  CTTATTAGTG  ACAAACATTA  CGTGATGAAC     420
ATGTCCAAGA  TCGATTCTAG  AGTAACAGGA  TCTTCCCTCC  TTAAGAAGGT  TAGCGAATGG     480
ACTGAAATGA  GAATGAACTC  CAACTTTAAT  GGAACATTTG  AACCATCAAG  ACTCGCCCTC     540
TCCAACTCTG  GCATGACAAC  GGCAGGAGTC  AACCTCGACG  TTATTGTCAA  ACCAAATAAT     600
GCAAGAAGTG  TACTAGGAAT  ATTGGAATGT  CATCGCCAGC  ACGTGTGCAC  CGCCGACGCC     660
AAGGGAACTG  TCGCTTCAGC  CATGCCAGCC  GTCTTCCAGG  CAACCGATGG  AAACGGTAAC     720
GAATCTGAAC  TGATCCAGAA  TGCTCTGCCA  AGGAACAGAT  ACATCCAAAA  GAGCACAATG     780
AACGCTCAAA  CTGTCGTGTT  TGCTAATGTT  TTGGAACAAC  TTATCGCCGA  TCTTGGAAAG     840
GTTATCGTGA  ACGAACTGGC  CGGCACCATC  GCTGAATCTG  TACCAGAAAG  CGTATATGAA     900
AACACCAAGG  AAATGATTGA  TAGACTAGGC  TCTGACGACC  TCTTCAAATC  TAATAATAAT     960
GGAGGAGTAG  AATCAATGGA  TTATGAAGAT  AGCGAAACAA  CATCCAACAA  TGGTCCCGTC    1020
CTCATCTCAG  AAGCCATGAA  GAATGCCGTC  TATCACACAC  TAATTTCCGG  CAAGGCAGCT    1080
CGCCCGGAAA  ATGTACCATT  CGCCTCATGC  GCCAGCGGCC  CTCTCGCCTT  TGATTTCCTT    1140
CTGTCAAAGG  GAGATACATT  CGAAGAAAAG  AACGCCGAAC  AAGGTGCAGC  AGCTGCCGTA    1200
TCCTCTACCT  ATTCTTCCTC  TTCTAACACT  ACTCTTCGTA  AGCATTTGGC  TCGAGTTTTC    1260
GAAGCCATCT  CTAAGCAAGT  AACTGATGCT  GAATTCAAGG  ATATCCTCAA  CGATATCGAA    1320
CGTAATATTT  CTTCTGACTA  TACTAACTGT  CCACCAAATA  CTAACCAAAA  TGCCTTTGCT    1380
CTAGCTATCA  AGAGAGAATT  CAGCAGAATT  GTTTCCTTCT  TAACCATTCT  TCGTAAGAAC    1440
ATTACACCCG  CATTAGTCGA  C                                                 1461
```

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
ACTACTAACT  TCAGCCTATC  TAG                                                 23
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TAATGCGGGT GTAATGTTCT TACGA                                          25

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GTAACTGCCC CTTCCATCTC CA                                           22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TACGGCAGCT GCTGCACCTT GT                                           22

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGGGAAGATA TGGGGACGAA T                                             21

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CGAAGAGTAG TGTTAGAAGA GGA                                          23

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AGAAGGTTAG CGAATGGACT G                                             21

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (x i) SEQUENCE DESCRIPTION: SEQ ID NO:9:

TTGAAGAGGT CGTCAGAGCC T    21

(2) INFORMATION FOR SEQ ID NO:10:

(i) SEQUENCE CHARACTERISTICS:
    (A) LENGTH: 23 base pairs
    (B) TYPE: nucleic acid
    (C) STRANDEDNESS: single
    (D) TOPOLOGY: linear (x i) SEQUENCE DESCRIPTION: SEQ ID NO:10:

GAAACGGTAA CGAATCTGAA CTG    23

(2) INFORMATION FOR SEQ ID NO:11:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:11:

CAGTCCATTC GCTAACCT    18

(2) INFORMATION FOR SEQ ID NO:12:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (x i) SEQUENCE DESCRIPTION: SEQ ID NO:12:

CGTCCCCATA TCTTCCCA    18

(2) INFORMATION FOR SEQ ID NO:13:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (x i) SEQUENCE DESCRIPTION: SEQ ID NO:13:

TGCCTTATCA GCTNTCGATT GTAG    24

(2) INFORMATION FOR SEQ ID NO:14:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (x i) SEQUENCE DESCRIPTION: SEQ ID NO:14:

TTCAGNTTTG CAACCATACT TCCC    24